(12) United States Patent
Bellotti et al.

(10) Patent No.: US 10,126,271 B2
(45) Date of Patent: Nov. 13, 2018

(54) APPARATUS AND METHOD FOR NON-DESTRUCTIVE TESTING OF MATERIALS

(71) Applicants: Aldo Bellotti, Charlotte, NC (US); Ralph N. Strayhorn, IV, Charlotte, NC (US); Amadeo A. Bellotti, Atlanta, GA (US)

(72) Inventors: Aldo Bellotti, Charlotte, NC (US); Ralph N. Strayhorn, IV, Charlotte, NC (US); Amadeo A. Bellotti, Atlanta, GA (US)

(73) Assignee: NLA Diagnostics LLC, Charlotte, NC (US)

( * ) Notice: Subject to any disclaimer, the term of this patent is extended or adjusted under 35 U.S.C. 154(b) by 0 days.

(21) Appl. No.: 14/855,208

(22) Filed: Sep. 15, 2015

(65) Prior Publication Data

US 2017/0074830 A1 Mar. 16, 2017

(51) Int. Cl.
| | |
|---|---|
| *G01N 29/04* | (2006.01) |
| *G01M 7/08* | (2006.01) |
| *G01N 29/11* | (2006.01) |
| *G01N 29/12* | (2006.01) |

(Continued)

(52) U.S. Cl.
CPC ............ *G01N 29/045* (2013.01); *G01M 7/08* (2013.01); *G01N 3/30* (2013.01); *G01N 29/043* (2013.01); *G01N 29/11* (2013.01); *G01N 29/12* (2013.01); *G01N 3/34* (2013.01); *G01N 2203/0039* (2013.01); *G01N 2291/014* (2013.01); *G01N 2291/015* (2013.01); *G01N 2291/0231* (2013.01); *G01N 2291/0421* (2013.01);

(Continued)

(58) Field of Classification Search
CPC .... G01N 29/045; G01N 29/043; G01N 29/11; G01N 29/12; G01N 3/00; G01N 3/32; G01N 3/34
USPC ........................................................ 73/12.12
See application file for complete search history.

(56) References Cited

U.S. PATENT DOCUMENTS 3,106,838 A * 10/1963 Crooks ................... G01M 7/08
                                                    73/582
3,580,056 A   5/1971  Warner
3,616,682 A  11/1971  Golis et al.

(Continued)

FOREIGN PATENT DOCUMENTS

| EP | 1892525 | 2/2008 |
|---|---|---|
| JP | 2006029946 | 4/1995 |
| WO | 2010150109 | 12/2010 |

OTHER PUBLICATIONS

International Atomic Energy Agency. "Guidebook on Non-Destructive Testing of Concrete Structures." Training Course Series No. 17, Vienna, 2002.

(Continued)

*Primary Examiner* — Manish S Shah
*Assistant Examiner* — Timothy Graves
(74) *Attorney, Agent, or Firm* — Nelson Mullins Riley & Scarborough LLP

(57) ABSTRACT

A device for testing a test material for defects within the test material has an acoustic broadband transducer offset from the test material surface during testing by a distance so that the transducer acquires acoustic waves across an air gap from the test material, wherein the acoustic waves arise from impact of an impact member on the test material.

23 Claims, 9 Drawing Sheets

(51) Int. Cl.
*G01N 3/30* (2006.01)
*G01N 3/34* (2006.01)

(52) U.S. Cl.
CPC .......... *G01N 2291/0422* (2013.01); *G01N 2291/0423* (2013.01); *G01N 2291/2694* (2013.01)

(56) References Cited

U.S. PATENT DOCUMENTS

| | | |
|---|---|---|
| 3,967,498 A | 7/1976 | Pezzillo |
| 4,023,396 A | 5/1977 | Yakshin et al. |
| 4,470,293 A | 9/1984 | Redmon |
| 4,519,245 A | 5/1985 | Evans |
| 4,615,209 A | 10/1986 | Change, Jr. |
| 4,682,490 A | 7/1987 | Adelman, et al. |
| 4,799,375 A | 1/1989 | Lally |
| 4,918,988 A * | 4/1990 | Ebihara ............ G01M 7/08 73/12.09 |
| 5,003,811 A | 4/1991 | Shannon et al. |
| 5,025,655 A | 6/1991 | Umemura et al. |
| 5,048,320 A | 9/1991 | Mitsuhashi et al. |
| 5,122,993 A | 6/1992 | Hikita et al. |
| 5,165,270 A | 11/1992 | Sansalone et al. |
| 5,404,755 A | 4/1995 | Olson et al. |
| 5,490,411 A | 2/1996 | Hogan |
| 5,614,670 A | 3/1997 | Nazarian et al. |
| 5,686,652 A | 11/1997 | Pfund |
| 5,748,758 A * | 5/1998 | Menasco, Jr. ......... H04R 23/00 381/173 |
| 5,814,731 A | 9/1998 | Alexander et al. |
| 6,026,686 A | 2/2000 | Hattori et al. |
| 6,112,599 A | 9/2000 | Maki, Jr. |
| 6,239,867 B1 * | 5/2001 | Aggarwal ............. G01N 21/87 356/30 |
| 6,301,967 B1 | 10/2001 | Donskoy et al. |
| 6,429,802 B1 | 8/2002 | Roberts |
| 6,581,466 B1 | 6/2003 | Costley et al. |
| 6,598,485 B1 | 7/2003 | Lin et al. |
| 6,684,681 B1 | 2/2004 | Zombo |
| 6,748,791 B1 | 6/2004 | Georgeson et al. |
| 7,036,605 B2 | 5/2006 | Suzuki et al. |
| 7,106,869 B2 | 9/2006 | Kanda et al. |
| 7,121,136 B2 | 10/2006 | Tsujii et al. |
| 7,367,236 B2 | 5/2008 | Georgeson et al. |
| 7,412,870 B2 | 8/2008 | Brankov |
| 7,516,646 B2 | 4/2009 | Makimoto et al. |
| 7,668,667 B2 | 2/2010 | Robb et al. |
| 7,900,498 B1 | 3/2011 | Ratcliffe |
| 7,963,919 B2 | 6/2011 | Proulx et al. |
| 8,079,265 B2 * | 12/2011 | Brignac ............... G01N 29/226 73/618 |
| 8,327,709 B2 | 12/2012 | Daraio et al. |
| 8,490,493 B2 | 7/2013 | Milmann et al. |
| 8,515,702 B2 | 8/2013 | Daw et al. |
| 8,567,252 B2 | 10/2013 | Fisk |
| 8,701,494 B1 | 4/2014 | Saxena et al. |
| 8,996,319 B2 | 3/2015 | Cokonaj |
| 2002/0183942 A1 | 12/2002 | Lafleur et al. |
| 2007/0034009 A1 | 2/2007 | Pado |
| 2009/0043516 A1 | 2/2009 | Liu et al. |
| 2009/0143681 A1 | 6/2009 | Jurvelin et al. |
| 2010/0286527 A1 | 11/2010 | Cannon et al. |
| 2010/0312496 A1 | 12/2010 | Armitage |
| 2013/0060140 A1 | 3/2013 | Sinelnikov |
| 2013/0073246 A1 | 3/2013 | Sprague |
| 2013/0178915 A1 | 7/2013 | Radziemski et al. |
| 2013/0250719 A1 | 9/2013 | Kollgaard et al. |
| 2013/0276539 A1 | 10/2013 | Wagner et al. |
| 2013/0286778 A1 | 10/2013 | Kisner et al. |
| 2014/0056104 A1 | 2/2014 | Buechler et al. |
| 2014/0311244 A1 | 10/2014 | Armitage |
| 2016/0011088 A1 * | 1/2016 | Guthrie ............... G01N 29/045 73/12.13 |

OTHER PUBLICATIONS

Pristov, E., Dalton, W., Piscsalko, G., and Likins, G. "Comparison of Impact-Echo with Broadband Input to Determine Concrete Thickness." Proc. NDE Conference on Civil Engineering, Aug. 2006, pp. 254-261.
Gibson, A. and Popovics, J.S., 2005 "Lamb Wave Basis for Impact-Echo Method Analysis," Journal of Engineering Mechanics (ASCE), vol. 131, No. 4, Apr. pp. 438-443.
ASTM C597-09, "Standard Test Method for Pulse Velocity Through Concrete."
NDT Instruments: BondMaster 600, "BondMaster 600 Multimode Bond Tester." http://www.olympus-ims.com/en/bondmaster600.
Carino, N.J. "The Impact-Echo Method: An Overview." National Institute of Standards and Technology, May 21, 2001.
Haroon, Muhammad, et al. "Implementation of Nonlinear Acoustic Techniques for Crack Detection in a Slender Beam Specimen." Proc. of SPIE vol. 6935, 2008 SPIE Digital Library.
Field Instruments for Nondestructive Evaluation of Concrete & Masonry. Impact-Echo Instruments, LLC, Aug. 2005.
Engholm, Marcus. "A Narrowband Ultrasonic Spectroscopy Technique for the Inspection of Layered Structures." Universitetstryckeriet, Uppsala, Aug. 2006.
Olson Instruments: NDE 360 Nondestructive Testing Platform. www.olsoninstruments.com, Mar. 4, 2014.
Ageeva, Victoria, et al. "Integrative Solution for In-situ Ultrasonic Inspection of Aero-engine Blades Using Endoscopic Cheap Optical Transducers (CHOTs)." 5th International Symposium on NDT in Aerospace, Nov. 13-15, 2013, Singapore.
Standard Test Method for Pulse Velocity Through Concrete, ASTM Designation: C 597-83 (Reapproved 1991).
Standard Test Method for Measuring the P-Wave Speed and the Thickness of Concrete Plates Using the Impact-Echo Method, ASTM International Designation: C1383-04 (Reapproved 2010).
Zhu, Jinying. "Non-Contact NDT of Concrete Structures Using Air-Coupled Sensors." University of Illinois at Urbana-Champaign, 2005.
Hoegh K., Khazanovich L., Yu H.T. "Ultrasonic Tomography Technique for Evaluation of Concrete Pavements." Transportation Research Record: Journal of the Transportation Research Board, No. 2232, pp. 85-94. 2011.
Malhotra, V.M., Carette, G.G., Carino, N.J., Naik, T.R., Henderson, G.D., Basheer, P.A.M., Long, A.E., Sivasundaram, V., Samarin, A., Lauer, K.R., Mitchell, T.M., Clemeña, G.G., Wiel, G.J., Mindess, S. "Handbook on Nondestructive Testing of Concrete." CRC Press. Jan. 2004.
ACI 318-11, "Building Code Requirements for Structural Concrete and Commentary." American Concrete Institute, Farmington Hills, MI. Aug. 2011.
Hartsuijker, C., Welleman, J., "Engineering Mechanics vol. 2." Springer, 2001. Chapters 1 and 9. ISBN 978-1-40 (e-book).
Army—Department of Defense solicitation—A12a-T013—Proposal Submission Instructions.
NLA Diagnostics, LLC Proposal to Department of Defense solicitation—A12a-T013.
Sixth Month Progress Report—Final Report.
NLA Defender specifications sheet.
Fifth Month Progress Report.

* cited by examiner

APPARATUS AND METHOD FOR NON-DESTRUCTIVE TESTING OF MATERIALS

BACKGROUND

The present invention relates to the use of acoustic waves in the non-destructive testing of materials.

Methods and devices are known that utilize the propagation and reception of acoustic waves for testing characteristics of materials used in the formation of a variety of products, for example rotary wings, aircraft fuselages, nacelles, aircraft control surfaces, honeycomb sandwich structures, composite turbine fan blades, automotive passenger cells, automotive body panels, sailboat spars and masts, and boat hulls.

Carbon fiber-reinforced polymer (CFRP) materials and structures are of increasing importance in the aerospace, automotive, and other industries, due to their light weight and high strength. In modern aircraft, the fuselage and wings can be made from more than 50% composite materials, for example based on carbon fiber sheets and/or including sandwich structures formed by carbon fiber composite sheets disposed on opposing outer surfaces of an aluminum honeycomb center structure. As should be understood in this art, other composite structures may be used, for example formed by fiberglass sheets on opposing sides of a NOMEX core. The strength of such composite materials may be compromised by degradation caused, for example, by impact damage, fatigue, and thermal damage during service, as well as defects created by faulty manufacturing. Defects may include delamination of a composite sheet forming one or the other side of a sandwich structure or bond failure between a core material (for example, the aluminum honeycomb or NOMEX cores discussed above) and the outer composite sheets (disbonding). Such defects are often not identifiable by visual inspection.

To determine these defects in such materials, it is known to place a transducer on the material and strike the material with an impact hammer to thereby generate mechanical waves in the material that are detected by the transducer. The transducer outputs a corresponding signal to circuitry that digitizes the signal and converts the signal to the frequency domain, and a processor analyzes the resulting data for signal structures indicating a defect. It is also known to house a piezoelectric transducer in a hand-held housing so that when the housing is placed against the test material, a surface of the piezoelectric transducer abuts the outer surface of the test material. It is necessary to maintain the piezoelectric transducer in highly direct acoustic contact with the material surface, and an acoustic coupling gel may be disposed on the transducer surface and in direct contact with the material surface for this purpose. Upon the user's actuation of a controlling processor, the processor actuates the piezoelectric transducer, causing the transducer to impart an acoustic signal into the test material and the processor to receive a resulting signal from the output of the piezoelectric transducer. The processor analyzes the resulting signal to identify presence of defects in the material.

The present disclosure recognizes and addresses the foregoing considerations, and others, of prior art constructions and methods.

SUMMARY OF THE INVENTION

A device protesting a test material for defects within the test material according to an embodiment of the present invention has a housing, an acoustic broadband transducer housed by the housing, and an engagement portion of the housing defined with respect to the acoustic broadband transducer so that a distal end of the engagement portion defines a surface that is offset from a receiving portion of the acoustic broadband transducer. An impact member defining an impact portion and being is housed by the housing so that the impact portion is moveable from a retracted position to the surface. The surface is offset from the receiving portion of the acoustic broadband transducer by a distance at which the acoustic broadband transducer is capable of acquiring acoustic waves across and air gap from a test material at the surface. The acoustic waves arise from impact of the impact portion of the impact member with the test material upon movement of the impact portion of the impact member to the surface. A processor system is in communication with the impact member and the acoustic broadband transducer so that the processor system, in response to receipt of an actuation signal, actuates the impact member to drive the impact portion from the retracted position to the surface, and so that the processor system receives a first output signal from the acoustic broadband transducer corresponding to the acoustic waves that arise from impact of the impact portion with the test material at the surface.

In a method of testing a test material for defects within the test material in an embodiment of the present invention, a test device is provided having a housing, an acoustic broadband transducer housed by the housing, and an engagement portion of the housing defined with respect to the acoustic broadband transducer so that a distal end of the engagement portion defines a surface that is offset from a receiving portion of the acoustic broadband transducer. An impact member defining an impact portion is housed by the housing so that the impact portion is moveable from a retracted position to the surface. The surface is offset from the receiving portion of the receiving broadband transducer by a distance. The test device is placed so that the engagement portion engages a test material at the surface. The impact portion of the impact member is moved to the surface so that the impact portion of the impact member impacts the test material. The acoustic broadband transducer acquires acoustic waves across an air gap from the test material. The acoustic waves arise from impact from the impact portion of the impact member with the test material.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, directed to one of ordinary skill in the art, is set forth in the specification, which makes reference to the appended drawings, in which.

Figure 1A:
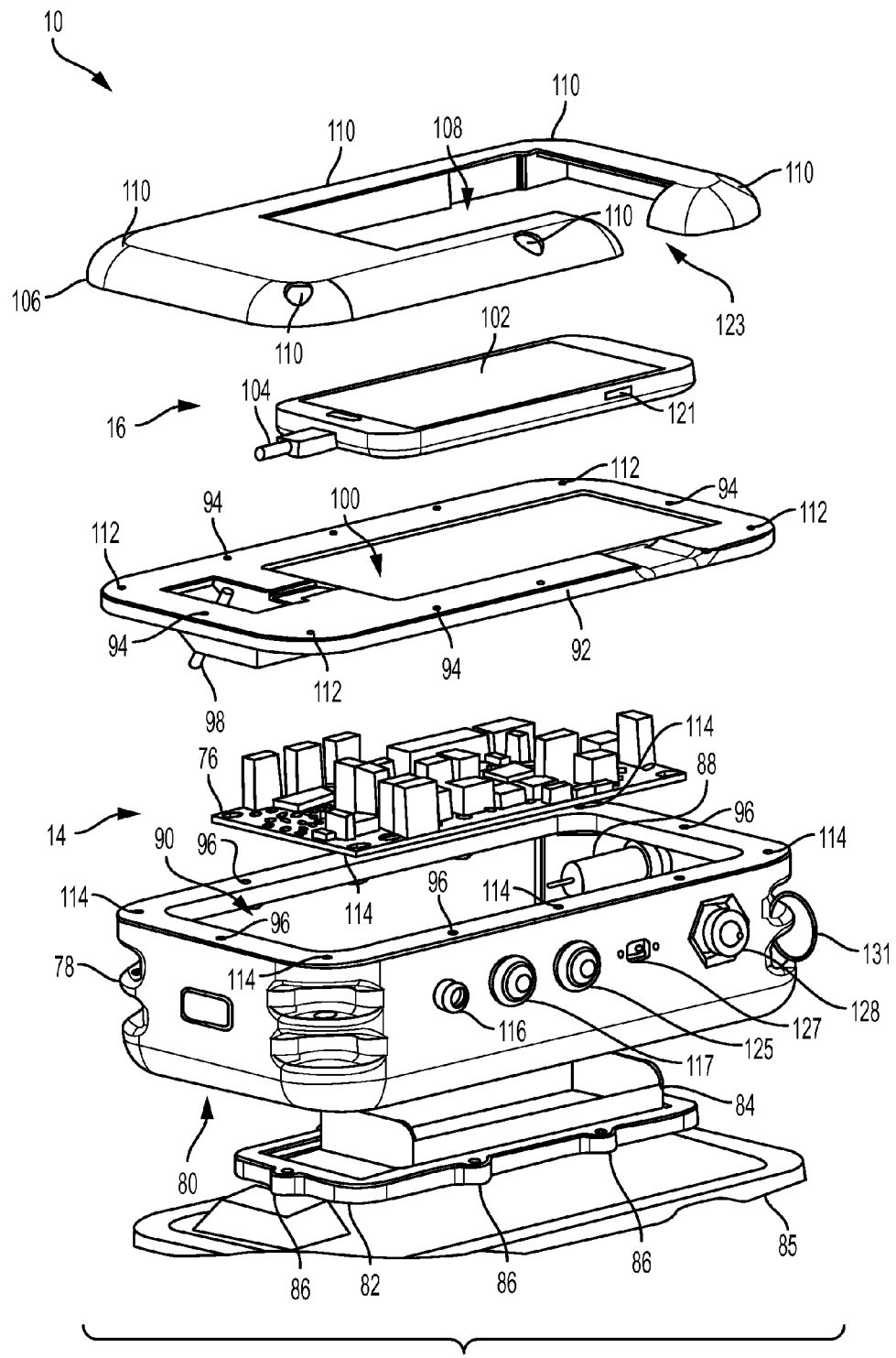
FIG. 1A is a perspective exploded view of a data acquisition unit and processor unit of a device for determining the presence of defects in a test material according to an embodiment of the present invention.

Repeat use of reference characters in the present specification and drawings is intended to represent same or analogous features or elements of embodiments of the present invention.

DETAILED DESCRIPTION OF PREFERRED EMBODIMENTS

Reference will now be made in detail to one or more embodiments of the present invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the present disclosure.

As used herein, terms referring to a direction, or a position, such as but not limited to "vertical," or "horizontal," "upper," refer to the meaning of those terms with respect to the Earth and others, such as "lower," "above," or "below," with respect to the signal acquisition unit, refer to directions and relative positions with respect to the unit's orientation in its normal intended operation when engaging a horizontal test surface. Thus, such terms should be understood in that context, even with respect to a signal acquisition unit that may be disposed in a different orientation.

Further, the term "or" as used in this application and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on."

The phrase "in one embodiment," as used herein does not necessarily refer to the same embodiment, although it may.

Figure 1B:
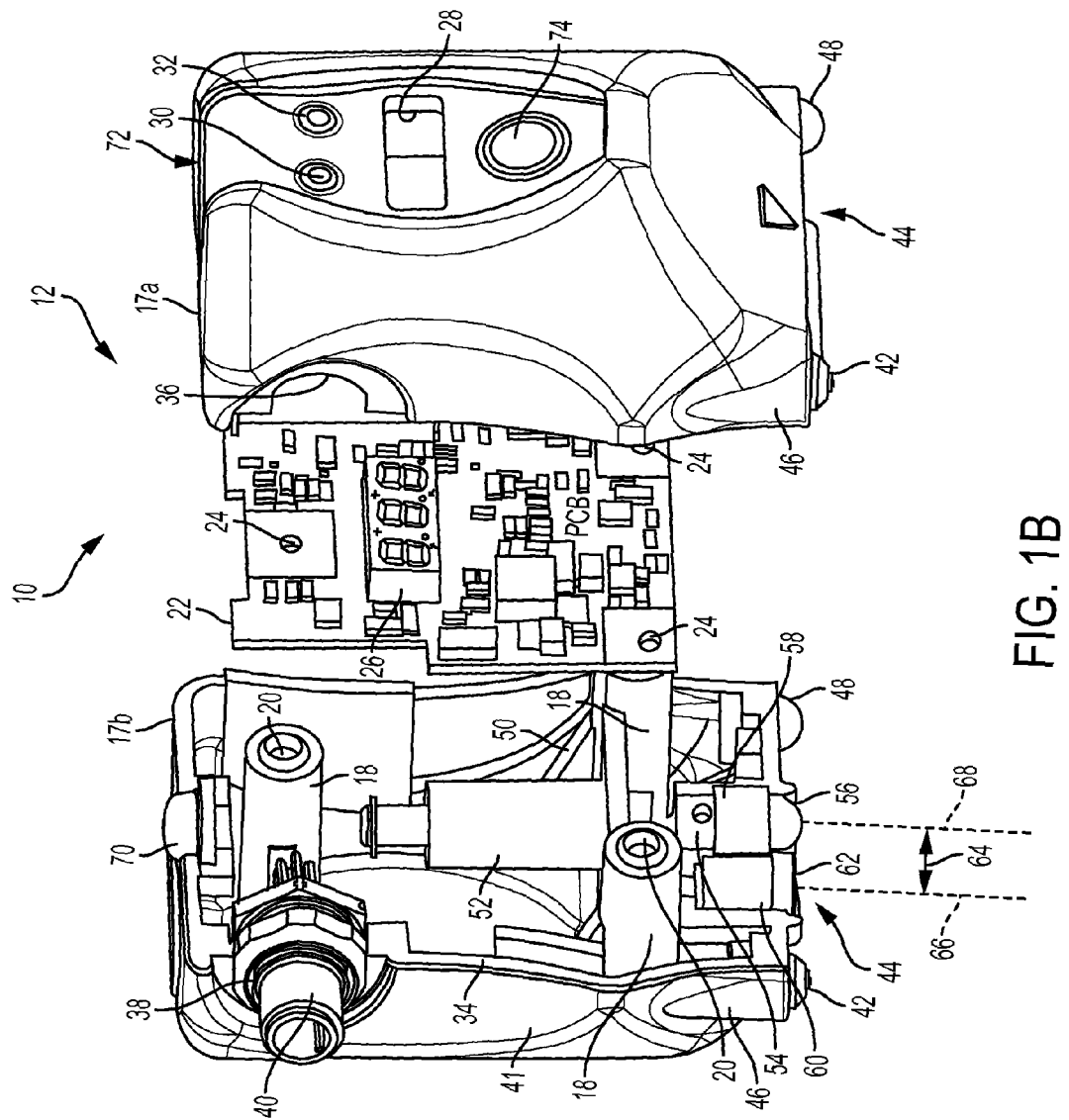
FIG. 1B is a perspective exploded view of a signal acquisition unit for use with the data acquisition unit and processing unit of the device as shown in FIG. 1A as part of the device for determining the presence of defects in a test material.
Figure 1C:
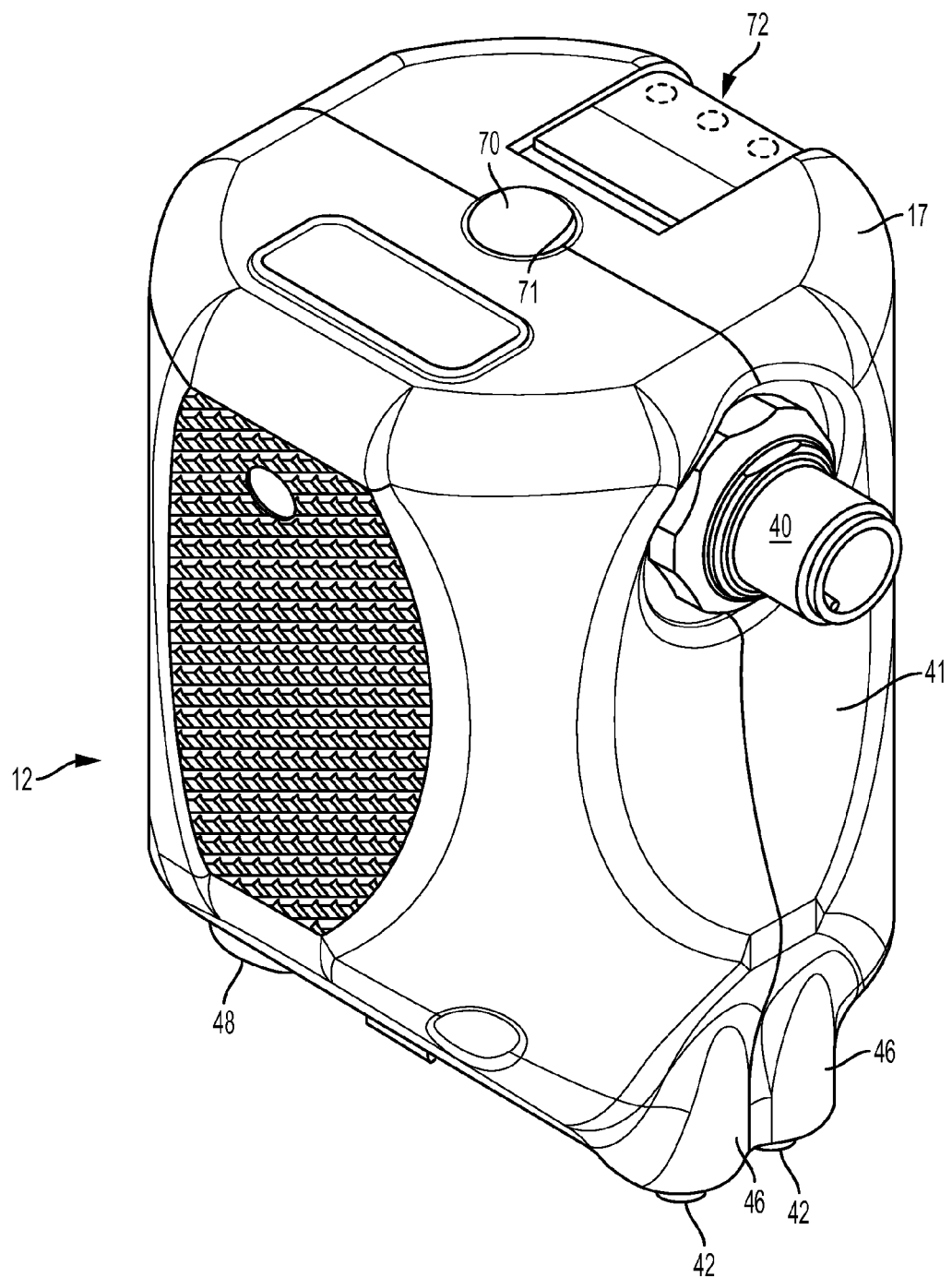
FIG. 1C is a perspective view of the signal acquisition unit as shown in FIG. 1B.
Figure 1D:
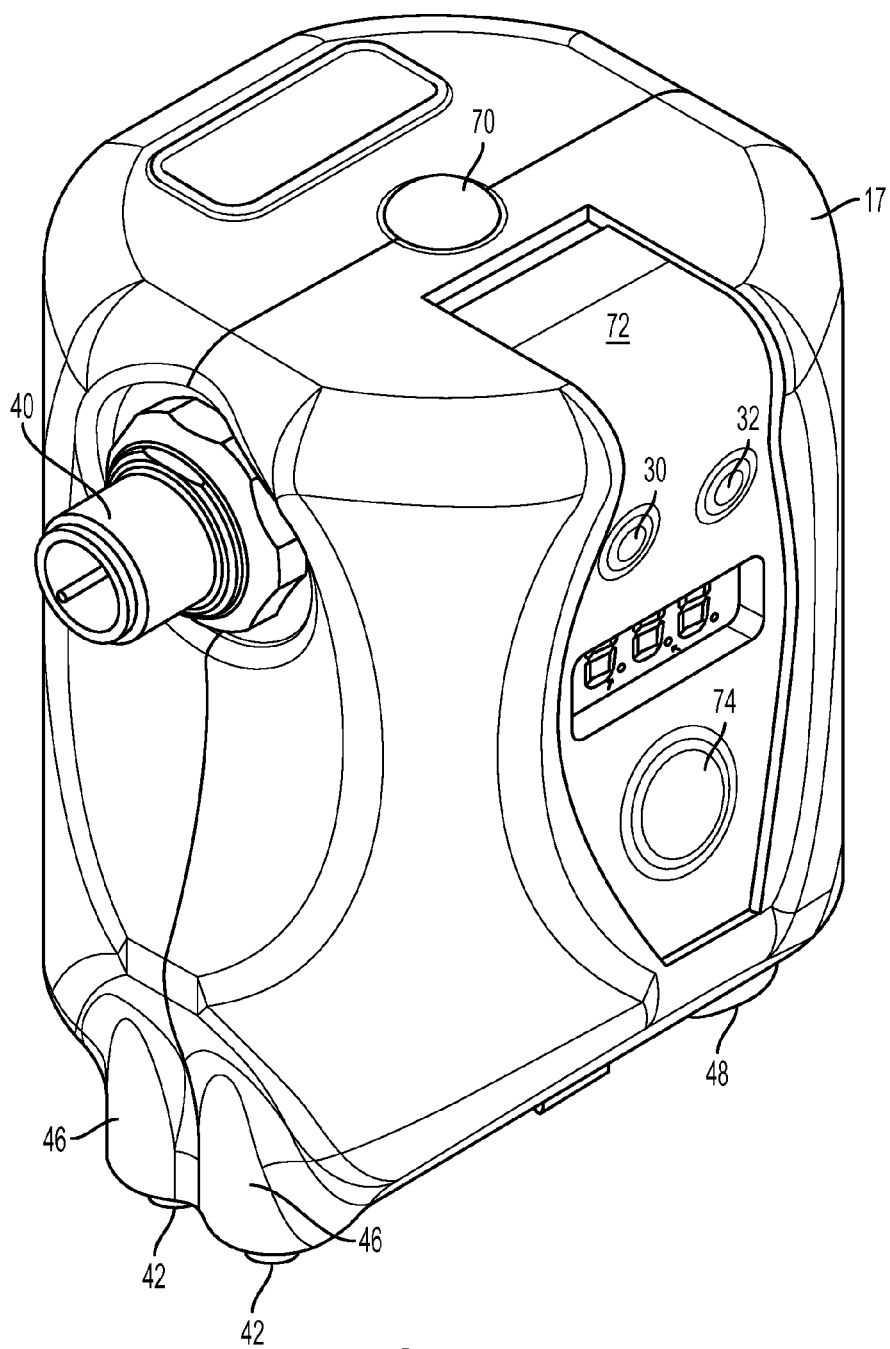
FIG. 1D is a perspective view of the signal acquisition unit as shown in FIG. 1B.
Figure 1E:
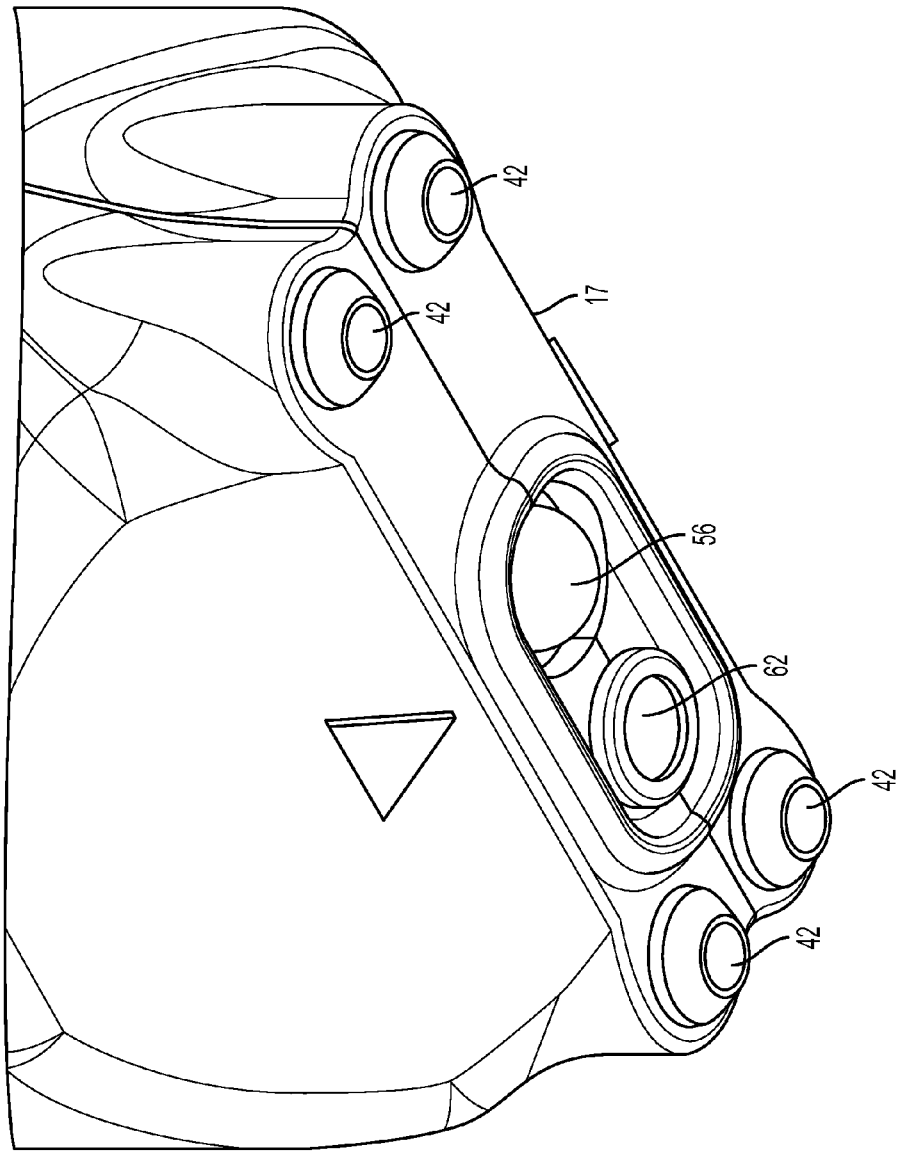
FIG. 1E a perspective view of the signal acquisition unit as shown in FIG. 1B having four rolling ball feet.
Figure 2:
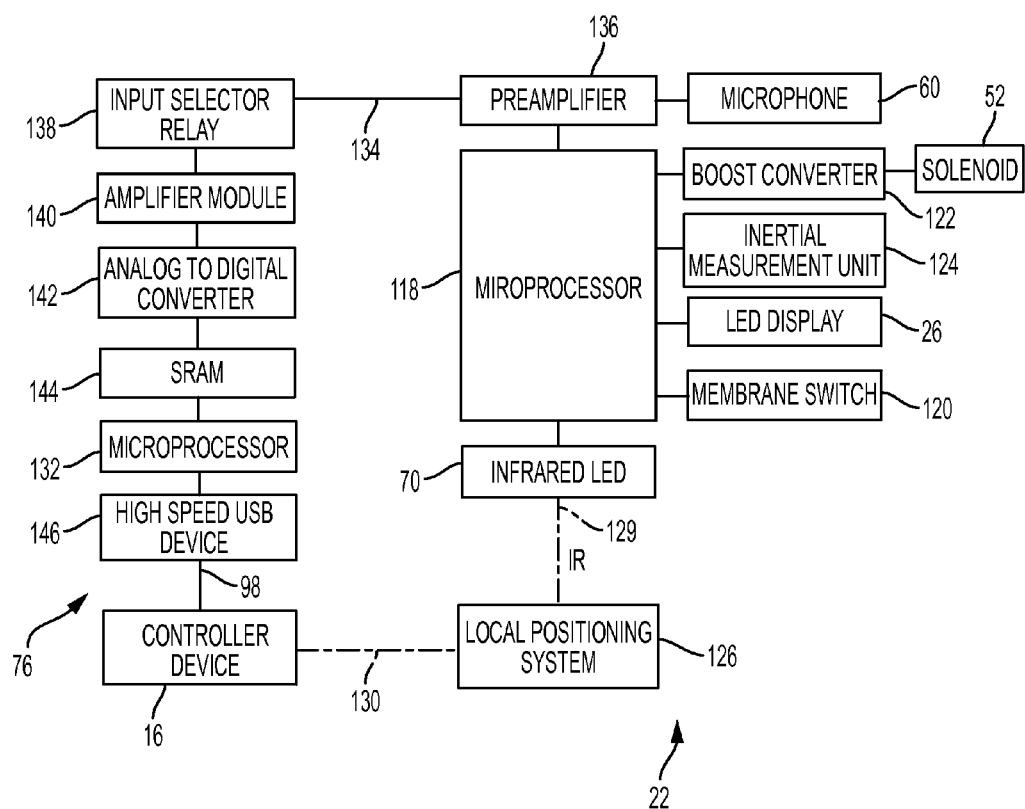
FIG. 2 is a schematic block diagram of control circuitry comprising the data acquisition unit and signal acquisition unit as in FIG. 1A and FIG. 1B.
Figure 5:
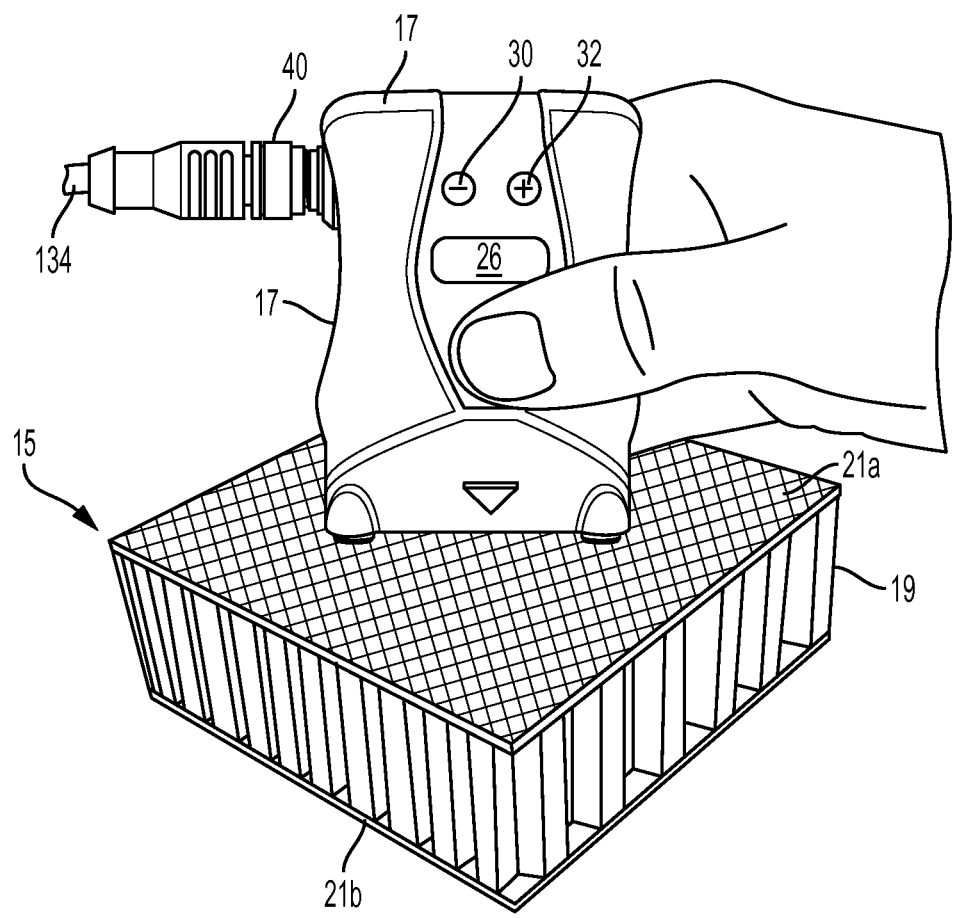
FIG. 5 is a perspective view of a signal acquisition unit as in FIGS. 1B-1E in use with a composite material that may be tested for presence of defects by the system, with the composite material shown in a sectional perspective view.

Referring to FIGS. 1A-1E, a hand-held device 10 for identifying defects in a composite material 15 (see FIG. 5), for example a wall of an aircraft engine or fuselage (for instance, an aluminum honeycomb structure 19 sandwiched between respective top and bottom CFRP composite sheets 21a and 21b, as shown in FIG. 5), includes a signal acquisition unit 12, a data acquisition unit 14, and a controller or processing unit 16. Referring particularly to FIGS. 1B and 1C, signal acquisition unit 12 includes a clamshell type construction defining opposing halves 17a and 17b, each made from a glass-filled NYLON 12 or other suitable thermoplastic or other material that forms a water tight device housing by a molding or other suitable process. Clamshell half 17b defines three connecting bosses 18, each defining a respective aperture 20 surrounded by a corresponding gasket. A circuit board 22 defines three holes 24 that respectively align with holes 20 and bosses 18 so that when board 22 rests upon the distal ends of bosses 18, holes 24 align with holes 20. Clamshell half 17a includes three pins (not shown) disposed correspondingly to holes 20 and 24 so that when mold half 17a is fitted to mold half 17b, the pins extend through holes 24 and into holes 20, securing the clamshell halves together. A shoulder surface and corresponding gasket (not shown) about each pin at clamshell half 17a abuts board 22 about the respective holes 24 so that, when clamshell halves 17a and 17b are assembled, board 22 is held securely in place between the clamshell halves. Referring also to FIG. 2, circuitry indicated at 22 in FIG. 2 is disposed on board 22 as shown in FIG. 1B, including an LED display 26 that, when unit 12 is assembled, extends through an aperture 28 in clamshell half 17a. A pair of push buttons 30 and 32 are secured in clamshell half 17a above aperture 28. As described in more detail below, these buttons communicate with circuitry on board 22 to provide a mechanism by which the operator may increase and decrease impact strength of a hammer mechanism held by clamshell half 17b.

Corresponding outer edges of clamshell half 17a and 17b mate with each other to thereby form a closed interior volume in which the components discussed herein are housed. A gasket 34 lines the edge of clamshell half 17b to form a water tight seal with the corresponding outer edge of half 17a. A similar gasket is provided about the edge of aperture 28 to sealingly engage LED display 26. A cut out portion 36 of clamshell half 17a mates about a correspondingly curved surface 38 of a LEMO, TURCK or other suitable cable connector 40. A gasket is provided about surface 38 to maintain the seal between the clamshell halves. When unit 12 is assembled, connector 40 extends a cable 134 (see FIGS. 2 and 5) connecting to it in a horizontal direction, or in a direction transverse to axes 66 and 68 (discussed below) of the device transducer and hammer. More generally, connecter 40 is disposed, and extends cable 134 from, a side 41 of housing 17 of signal acquisition unit 12 that is transverse to a lower face 44 of unit 12.

Each clamshell half holds a respective rolling ball bearing bolster 42 extending from lower face 44 of signal acquisition unit 12. The ball in each bolster 42 is secured axially in its respective bolster housing 46 so that the ball may roll freely about any axis but may not move vertically within the bolster housing. Thus, the two balls 42 define feet of unit 12 that engage the material surface under test by unit 12. Each clamshell half also defines a respective non-rolling bolster 48 formed in a semi-spherical shape with an outer (lower, in the perspective of FIG. 1B) surface covered with or made of a low-friction material, for example DELRIN, capable of sliding on the expected test material. The vertical distance from face 44 to the distal ends of feet 48 is the same as the vertical distance from face 44 to the distal ends of ball feet 42 so that, when signal acquisition unit 12 is disposed on the bolsters on a planar surface, the broadband transducer (a microphone, as described below) surface is disposed in a parallel position above the test material surface. The bolsters/feet define an engagement portion of the housing of signal acquisition unit 12 in that they engage the test material surface (see the surface of upper composite sheet 21*a*, in FIG. 5) when the unit is in operation for a test, as shown in FIG. 5. The four distal ends of bolsters 42/48 define a plane. While the actual test material surface the bolsters engage for a test may, as described below, vary from a planar configuration, the bolster ends may be considered to define a planar surface for purposes of discussing the configuration of unit 12 herein. Although this embodiment includes two rolling ball-type bolsters 42 and two non-rolling bolsters 48, it should be understood that other configurations are possible, e.g. four non-rolling bolsters or four rolling ball bolsters, and FIG. 1E illustrates the signal acquisition unit of FIGS. 1B-1D having four rolling ball bolsters 42.

A bracket 50 secured within clamshell half 17*b* secures a connecting boss between the clamshell halves. A further bracket secures a solenoid unit 52 that drives a hammer 54, as described in more detail below. The housing of solenoid 52 secures a spring that engages hammer 54 to thereby bias hammer 54 upward, away from the test material surface (see the surface of composite material 21*a*, FIG. 5) and the surface defined by the bolster ends. Solenoid 52 also includes a coil surrounding an upper arm of hammer 54 that is selectively actuated, as described below, by delivery of electric current through the coil to thereby drive hammer 54 downward, against the spring bias, away from face 44 and toward the surface defined by the bolster ends so that a distal end, or impact portion, 56 strikes the test material surface located at the surface defined by the bolster ends. A TEFLON ring 58 surrounds an outer circumference of the lower portion of hammer 54 and is slidingly received within a correspondingly-shaped molded portion (not shown) of clamshell half 17*a* that acts as a guide to maintain up-and-down movement of hammer 54 and minimize vibrations from such movement.

A second bracket (not shown) in clamshell half 17*b* secures a microphone assembly 60 that defines a broadband receiving transducer surface 62 at face 44. Microphone 60 is an electronic condenser microphone having, in this embodiment, an acoustic bandwidth within range of about 2 kHz to about 25 kHz or to about 30 kHz. An example of such a microphone is provided by PUI Audio, Inc. of Dayton, Ohio, under part no. PUM-3564L-R. While the frequency range of 2 kHz to 30 kHz is discussed herein within the context of the presently-described embodiments, it should be understood that this is for purposes of example only and that the operative frequency range may vary depending upon the desired use of a given device. In general, and within the microphone/transducer operable frequency range, the ability to detect higher frequency acoustic signals within that operable frequency range requires that the system detect signals having correspondingly shorter wavelengths. This may, in turn, affect selection of the separation between the hammer and the microphone transducer. For instance, the p-wave that the microphone/transducer is intended to detect is generated by a signal originated by the hammer and that travels in the test material in directions generally along the hammer axis as indicated at 68. The p-wave's front width varies with wavelength. Accordingly, in certain embodiments, the hammer and the microphone transducer are disposed sufficiently close together that the system can detect the acoustic p-wave signals generated from impacts from the system's hammer at resonant frequencies within the full operative frequency range of the microphone/transducer, and more specifically at the high end of the transducer's operative frequency range, which corresponds to the short end of the wavelength range.

In the presently-described embodiments, microphone 60 and hammer 54 are disposed at face 44 so that they are separated by a center-to-center distance of about 0.5 inches. Orienting the device so that the hammer is directly over the defect during the test maximizes the likelihood of detecting the defect. In certain embodiments as described herein, where axes 66 and 68 respectively of microphone transducer 60 and hammer 54 (where axes 66 and 68 are parallel to each other and perpendicular to the transducer face) are separated by about 0.5 inches, the system can detect defects with widths (in a plane perpendicular to axes 66 and 68) of about 0.25 inches. Thus, where hammer 54 is directly over the defect, the microphone may be offset from the defect.

Clamshell half 17*b* secures an infrared transmitter 70 that is received in a corresponding cut out 71 (FIG. 1C) in a top portion of clamshell half 17*a*. Also on the top of clamshell 17*a* is an LED display 72 having LEDs capable of distinctly displaying the colors red, yellow, and green. A start-stop button 74 is provided on a front face of clamshell half 17*a*.

Referring also to FIG. 1A, data acquisition unit 14 comprises a circuit board 76, and associated circuitry disposed thereon, secured within a molded housing 78 made from a glass-filled NYLON 12 or other suitable thermoplastic. Housing 78 defines a lower face 80 having an aperture (not shown) into which fits a plate 82 to which is secured a tray 84 to receive one or more batteries (not shown), for example six "AA" type batteries. Plate 82 is secured by a plurality of screws (not shown) that extend through holes in bushing portions 86 in cap 82 and that are threadedly received in threaded female anchor portions (not shown) formed in or attached an interior portion of housing 78. A lower cap plate 85 covers the bottom of the unit.

The batteries (not shown) held by tray 84 provide power to the circuitry on board 76 and may provide power to processing unit 16. A fuse 88 is secured to an inner portion of housing 78 and communicates with a power circuit that includes the batteries in tray 84 and the circuitry disposed on board 76. Fuse 88 protects the components of the data acquisition unit and processor unit by disconnecting power flow from the batteries at high-current events, as should be understood. Housing 78 defines an open top end 90 over which fits a mobile device bracket 92 that is secured to an upper edge of housing 78 by screws (not shown) that extend through holes 94 and are threadedly received by corresponding threaded bores 96 along the edge of housing 78. An electrical conduit 98 extends through bracket 92 to allow electrical communication between processing unit 16 and data acquisition unit 14, as described below. Bracket 92 defines a recess 100 shaped to receive processing unit 16, which in this embodiment is a "smart phone" type mobile computing device having a processor and touch screen 102, as should be understood in this art. One example of a smart phone that may be used for this purposes is a GALAXY S4 ACTIVE available from Samsung Electronic Company, Ltd., of Yongin-si, Gyeonggi-do, Korea, although it should be understood that other processor-based circuitry may be used, including tablets and dedicated embedded circuitry. A jack 104 attached to the smart phone connects to a cable (not shown) that extends through conduit 98 to facilitate communications between a processor (not shown) of processing unit 16 and a processor of data acquisition unit 14. Processing unit 16 may operate from power provided by a battery internal to unit 16 or, optionally, from line power provided by a cable connection via an input port 121 from an external source or, as described below, from the data acquisition unit.

An upper cap plate 106 covers processing unit 16 and holds processing unit 16 within recess 100. Cap plate 106 defines an aperture 108 sized correspondingly to touch screen 102 and other control features on device 16 to provide user access to the touch screen and other controls. Cap plate 106 is secured to plate 92 and housing 78 by screws (not shown) that extend through holes 110 in cap plate 106 and corresponding through-holes 112 in plate 92 to be threadedly received in corresponding threaded bores 114 in housing 78.

A power connection port 116 is provided on a side of housing 78 to provide an optional access point at which to provide power from an external line power source to the circuitry of the data acquisition unit. When line power is applied to the unit via connector 116, actuation of a master/slave switch 117 causes circuitry on board 76 to draw power from line power connector 116 rather than from the batteries of tray 84. In another embodiment, circuitry on board 76 recognizes the presence of line power at 116 and responsively automatically draws power from the line power connector, rather than the batteries, without need for switch 117. In either arrangement, when applied to data acquisition unit, line power may supersede the battery power and may be provided to processing unit 16, as noted below, and to data acquisition unit 12 (via a power line in communication cable 134, as shown in FIGS. 2 and 5).

A USB port 127 disposed in the side of housing 78 communicates with the power circuitry that draws power from the batteries stored in tray 84 or line power from jack 116. The USB 2.0 port can receive an electrical cable that attaches at its other end at input port 121 of the smartphone of processing unit 16 that is accessible through a gap 123 provided in upper cap plate 106 so that the smartphone battery may be optionally recharged from the batteries of unit 14 or from line power. An on-off button 125 controls a switch that communicates with the circuitry of data acquisition unit 14 to activate and deactivate device 10, including data acquisition unit 14, processing unit 16, and signal acquisition unit 12. Button/switch 125 directly actuates actuation circuitry on board 76, the processor of which forwards actuation signals to units 16 and 12 via communication paths discussed below. Alternatively, the user may activate processing unit 16 through a control provided with the smartphone. An application on the smartphone, in turn, forwards an actuation signal to unit 14, which forwards an actuation signal to unit 12. A cable connector 128 receives the opposing end of a communication cable 134 (FIGS. 2 and 5) attached to cable connector 40 (FIG. 1B). Cable connector 128 electrically communicates with a processor of data acquisition unit 14, and cable connector 40 is in electrical communication with a processor of signal acquisition unit 12, so that the two processors communicate via the cable indicated at 134 in FIG. 2 and cable connectors 128 and 40.

The discussion herein makes reference to the user uploading data from, or possibly downloading data or software to, system 10 and particularly processing unit 16. While it should be understood that various mechanisms may be used from those purposes, in the presently illustrated embodiments the user uploads data from unit 16 to an independent computing system though a wireless Internet or other network connection (e.g. using BLUETOOTH or other protocol) from, or by a cable connected to a port of, processing unit 16. The user may upload data to, or download data or software from, the independent computer system directly or via an intermediate data storage provider. For such purposes, the user may interact with an application provided with and executed by processing unit 16 via touch screen 102, to select the desired data to upload to or download from the independent computer system. Under control of the application, and when the wireless connection is established or when the cable is connected to and between unit 16 and the independent computer system, processing unit 16 and the independent computer system communicate so that processing unit 16 recognizes the presence and availability of the independent computer system to receive or send the data or software. Processing unit 16 may be operated in this fashion while attached within the data acquisition unit housing but may also be removed from the housing and used separately from the data acquisition unit for data and software exchange, if desired. The protocols and programming methods for communication between such devices should be well understood and are, therefore, not discussed in further detail herein.

In the presently described embodiment, housing 78 is 8.6 inches in length by 5 inches in width, by 2.9 inches in height, and has a weight of approximately 1.75 pounds. These dimensions and weight facilitate a user's ability to carry housing 78, and therefore data acquisition unit 14 and processing unit 16, by hand while simultaneously operating signal acquisition unit 12, holding signal acquisition unit 12 in the user's other hand. The housing of signal acquisition unit 12 is about 3.6 inches in height, about 2.6 inches in general diameter (cable connector 40 extends about 1.6 inches from the SAU housing's center axis), and about six ounces in weight. The SAU is thus easily hand carried and hand actuatable, though it should be understood that the SAU's size and weight can vary. A cable (indicated at 134 in FIG. 2) extending between cable connectors 128 and 40 is approximately ten feet in length. Alternatively, a strap may be provided that attaches to a ring 131 secured to a corner of housing 78, so that the user may hang the data acquisition unit and processing unit over the user's shoulder by the strap while operating the signal acquisition unit with one hand and leaving the user's other hand free. Still further, ring 131 may be attached to a clip or other attachment device attached to the user's apparel.

As noted above, the distal ends of bolsters 42 and 48 (or of four bolsters 42 or four bolsters 48) define a planar surface that is parallel with the receiving surface of the broadband transducer of microphone 60 and is separate or offset from the microphone receiving surface by a distance, in this embodiment, of about 0.1 inches or greater. Because the microphone transducer receiving surface is offset from the material test surface by an air gap, as opposed to an intervening acoustic coupling material, the resulting acoustic impedance mismatch between the test material surface and the air gap lowers the signal power received by the microphone transducer, as compared to the signal power received by a transducer acoustically coupled to the test material surface by a coupling gel. The received power can be increased by reducing the air gap distance, but on the other hand, increasing the gap distance provides greater accommodation for surface irregularities. Thus, the particular air gap distance can vary to accommodate these and/or possibly other considerations. The air gap separation between the microphone transducer receiving surface and the expected test material surface position may be assumed, for design purposes, to be the distance along axis 66 between the transducer surface and the plane defined by the distal ends of bolsters 42 and 48. The ability of the signal acquisition circuitry to effectively acquire the acoustic signal radiated from the test material surface and distinguish that signal from noise may depend on factors such as the air gap distance, the signal acquisition circuitry's dynamic range (e.g. 48 dB in the present example), and the construction of the microphone. In a given design, the gap may be selected through testing of a particular device on test material surfaces to accommodate expected variations in the test material surface (as described in more detail below), while permitting the acquisition of a sufficient acoustic return signal to detect defects in the test material in view of the device's signal acquisition circuitry and the analysis algorithm used to detect the defect.

In the presently-described embodiments, and for purposes of example but not limitation, the system can identify material defects utilizing various suitable signal analysis methods, for example based on signal magnitude or frequency. As indicated above, an impact from the impact hammer may create multiple types of waves in the test material, for example, primary waves ("p-waves"), shear waves ("s-waves"), and Rayleigh waves ("r-waves"). As should be understood, p-waves and s-waves propagate into the solid material along spherical wave fronts, with the p-wave defining a compression wave pattern in the direction of the wave's propagation and the s-wave defining a wave that varies in a direction normal to the propagation direction. R-waves are surface waves that propagate outward from the impact point and that can also be created on the opposing side of the test surface by the p-waves and s-waves. It will also be understood that the speed at which the various types of waves propagate in a given material varies with respect to each other. Thus, for example, s-waves propagate at a speed slower than the speed at which p-waves propagate. Considering, for example, a composite material used in the construction of aircraft fuselages wings, control device surfaces, rotary blades, engine nacelles, radomes, and turbine fan blades, constructed of a carbon fiber-reinforced polymer composite sheet separated from a similar composite sheet by a honeycomb aluminum core sandwiched between and bonded to the opposing carbon fiber composite sheets, for example as illustrated in FIG. 5, any one or more of mechanical disbonding between the major layers of the material, delaminations within the composite sheets, crushing of all or a part of the aluminum core, thermal degradation and voids can cause the development of standing waves in the material arising from the various waves imparted to the material by the hammer. Standing waves can develop between the test material surface and the opposing surface and/or such defects. These standing waves can be detectible at their resonant frequencies or based on signal magnitude. The thickness of the test material for which the device as described herein can detect defects through the entire thickness will vary with the materials and construction of the test material, e.g. depending on the thickness and layers of the (for instance, carbon fiber) front and back surface sheets, the type of honeycomb inner material (e.g. aluminum or NOMEX), the honeycomb structure's thickness, and whether or not the test material is perforated.

Microphone 60 in these embodiments utilizes an electric condenser microphone transducer generally capable of detecting acoustic signals up to about 30 kHz, and in the presently-described embodiments the effective range of microphone 60 may be considered to be from about 2 kHz to about 25 kHz. At such a frequency range, the system comprised of the microphone and the processing circuitry that processes signals from the microphone operates at a resolution capable of detecting defects having a minimum dimension of about 0.5 inches by about 0.125 inches, or about 0.25 inches by about 0.25 inches, in an orientation transverse to the waves' travelling direction, or parallel to the transducer receiving surface. As described above, the microphone transducer can be offset from the test material surface, so that an air gap separates the two. Although either omnidirectional or unidirectional microphone transducers may be used, unidirectional transducers are used in the presently-described embodiments in testing composite materials having surfaces that are not perforated, while omnidirectional transducers are used with materials having perforated surfaces.

The data acquisition circuitry of unit 14 collects signal output data from microphone 60 (via signal acquisition unit 12) at a sampling frequency of about 500 kHz. For each impact of the test material surface by hammer 54, the circuitry of data acquisition unit 14 collects 1,024 data points for analysis (although, as noted below, the data collection rate may be changed in certain embodiments at the user's selection). Signal acquisition unit 12 preamplifies and uploads analog data to data acquisition unit 14, which digitizes the signal and uploads the digitized information to processing unit 16 for analysis by the application program that executes at unit 16. In one of the embodiments discussed herein, the application at unit 16 determines the maximum peak-to-peak voltage difference in the signal and compares that value to a predetermined primary threshold and a predetermined secondary threshold. In response to the comparison, the processing unit displays information describing the result at screen 102 and also sends an instruction to the data acquisition unit, which relays the instruction to the signal acquisition unit, to thereby cause the signal acquisition unit to activate one of the LEDs 72 at the top surface of unit 12. As discussed above, there are three colors of LEDs 72—green, yellow and red. If the peak-to-peak signal is above the primary threshold but below the higher, secondary threshold, the instruction causes the signal acquisition unit to actuate the yellow LED 72. If, however, the signal is above both the primary and secondary threshold levels, the signal causes the signal acquisition unit to actuate the red LED 72, indicating a significant defect. If the peak-to-peak voltage of the acquired signal is below the primary threshold, the instruction signal to the signal acquisition unit causes the signal acquisition unit to actuate the green LED 72, indicating a likelihood that a defect has not occurred.

To calibrate the system for amplitude-based signal analysis, the user selects a sample of the material that will be tested but that the user knows has no defects and places the signal acquisition unit onto the test material surface so that the distal ends of the bolsters engage the surface. The user begins a test through a "calibrate" button provided by the application's graphical user interface at screen 102 and starts the hammer and microphone either by actuating start/stop button 74 on unit 12 or activating a button in the graphical user interface provided by unit 16 on touch screen 102. This actuation signal causes the signal acquisition unit processor (in automation mode) to drive the hammer at a rate of about eight to about ten, and in this example eight, strikes per minute. Microphone 60 receives acoustic signals from the test material resulting from the hammer blows. Preamplifier 136 adjusts the analog signal level, and data acquisition unit 14 thereby receives the analog signal from the microphone via preamplifier 136 and cable 134. The circuitry of data acquisition unit 14 identifies the beginning of each signal spike (i.e. the beginning of each portion of the measurement signal corresponding to a hammer tap), and then acquires a number of data points (e.g. 1024, 2048, or 4096) at a sampling rate (e.g. 500 kHz) as selected by the user at step 150, as described herein with respect to FIG. 4. A default setting in these embodiments is 1024 data points at a sampling rate of 500 kHz, so that data acquisition unit 14 acquires and digitizes the analog measurement signal for an approximately two millisecond (2.048 millisecond) period following the detection of each incoming hammer tap. The collected digitized data for each two millisecond period is referred to herein as a test block of data. Processing unit 16 receives the digitized time-domain signal from data acquisition unit 14. The processing unit's processor, under control of the application, determines the peak-to-peak voltage of the digital signal for each received test block of data and displays the voltage on a display provided by touch screen interface 102 as the test blocks are received and processed by unit 16.

The particular value of the displayed output depends not only upon the signal data, but also upon the active range of the signal processing circuitry of data acquisition unit 14 and the gain applied to the acquired signal within that circuitry. In the present embodiments, the signal acquisition circuitry of data acquisition unit 14 has an active range from 0 mV to 850 mV. Thus, the peak-to-peak value determined by the application at unit 16 for each given test data block and displayed at screen 102 is a value between 0 and 850 mV peak-to-peak, as determined by the signal data and the gain that the circuitry of data acquisition unit 14 applies to that signal. The programming of the application executed by the processor of processing unit 16 compares the peak-to-peak voltage level of the acquired signal for each test data block to the predetermined (and stored, in memory of unit 16) primary threshold level and secondary threshold level, each defined in the application as a selectable mV level, or alternatively as a percentage of the device's overall active range. Depending on the comparison, the processing unit sends a signal to signal acquisition unit 12 via data acquisition unit 14 to actuate the corresponding red, green, or yellow LED 72. In this example, the predetermined primary threshold level is 500 mV, while the secondary threshold is 600 mV. In another embodiment, the secondary threshold is omitted, so that only the 500 mV primary threshold is used and so that only the green and red LEDs of LEDs 72 would be actuated.

At initiation of the calibration, signal acquisition unit 12 will have an existing gain and an existing hammer impact strength, for example set during the system's original configuration or by a previous calibration. Signal acquisition unit 12 actuates the hammer and applies the gain to the resulting signal received by microphone 60 and passed up to data acquisition unit 14, causing a display of the resulting peak-to-peak voltage at display 102 and the actuation of a green, yellow or red LED 72 (or green or red, if there is no secondary threshold or if it is optionally omitted) on signal acquisition unit 12, depending upon the result of the application of the signal peak value to the initialized 500 mV and 600 mV primary and secondary thresholds. The user first refers to LEDs 72 for an initial, rough calibration. If the signal results in actuation of a yellow or red LED (or, if no secondary threshold is used, a red LED), then the hammer impact strength is too high, in that the system is indicating a defect exists when in fact the material has no defects. The user, however, can change the impact hammer's impact strength through actuation of buttons 30 or 32 on the signal acquisition unit housing. These buttons are connected to a switch system that communicates with the signal acquisition unit microprocessor. The processor's programming is configured to recognize actuations of button 30 as a request to decrease the solenoid power, and to interpret actuations of button 32 as a request to increase the solenoid power. Thus, by pressing button 30, the user instructs the signal acquisition unit processor to lower the power at which hammer 54 taps the test material. Correspondingly, the user's actuation of button 32 instructs the signal acquisition unit processor to increase the hammer impact force. As the user moves the impact power up or down, the signal acquisition unit processor changes a display of the impact power rating on display 26.

In this instance, since the user knows that the system is indicating a defect (i.e. by a red or yellow LED at 72), when in fact the test material is known not to have defects, the user knows that the hammer impact strength is too high, and so actuates button 30 to lower the hammer impact power, and repeats the test. If the LED 72 again shows yellow or red, the user again lowers the hammer impact strength and repeats the process, continuing to do so until the test results in a green LED 72. At the point when the LED display goes from yellow (or red) to green, the user has set the impact strength so that the system's use with a sample of a test material of the type for which the calibration is performed that has no defects will result in a peak-to-peak signal at processing unit 16 just below 500 mV, and therefore a green LED output 72 at signal acquisition unit 12, while the system's use with such a sample having a defect will result in a peak-to-peak signal at processing unit 16 above 500 mV, and therefore a yellow or red LED output 72. Having achieved a hammer impact strength resulting in a peak-to-peak signal just below 500 mV for a sample having no defects, the user may then view the displayed numerical value of the peak-to-peak voltage on display 102 and continue to reduce impact hammer strength downward, if desired, to provide a buffer between a "normal" return signal and one that will trigger identification of a defect.

If the calibration signal initially results in a green LED 72, indicating that the return signal during the calibration test correctly indicates that no defect is present, the user actuates button 32 to increase the hammer impact strength and repeats the process until the acquired signal peak-to-peak voltage exceeds 500 mV, thereby changing the LED display 72 from green to yellow (or red, if no secondary threshold is used). At this point, the user views the actual voltage output on display 102, and actuates button 30 to lower the hammer impact strength, repeating the process until the return signal moves back below 500 mV peak-to-peak, thereby returning the LED display 72 to green, and possibly further if a buffer distance is desired.

If the user is unable to successfully calibrate the signal by adjusting hammer impact strength in this manner, or if, having made an initial calibration by adjusting hammer impact strength, the user wishes to make adjustments at a finer scale, the user may also make adjustments to the gain applied to the microphone output signal by preamplifier 136. To allow this functionality, the application operating on processing unit 16 provides a user interface option at display 102 through which the user may enter a numerical value for the desired pre-amplification level or select from a list of predetermined level options, the entry or selection of which causes the processor at processing unit 16 to communicate a signal to the processor of data acquisition unit 14, in turn causing that processor to instruct the processor of signal acquisition unit 12 to accordingly adjust the gain applied by the SAU's preamplifier 136 to the incoming microphone signal.

Additionally, the user may exchange the hammer 54 in the signal acquisition unit for one of greater or lesser mass/weight in order to apply a greater or lower impact force to the material, as test materials can provide varying responses to hammers of different mass. For example, even if the user has successfully calibrated the device using hammer impact force adjustment and/or gain adjustment, there may be a need to change hammers for a given test material if the contrast difference, i.e. the difference in the measurement signal peak-to-peak voltage when no defect is present and the peak-to-peak voltage when a defect is present, is either too large or two small. If, for example, with a hammer of a given mass, the contrast difference can range up to a high mV level (the difference is variable because different defects result in different voltage changes) as compared with the device circuitry's active range, the measurement signal could be too sensitive, giving false positives. If the contrast range is too small, some signals corresponding to defects could be masked by noise. In certain embodiments as described herein, it is desired that this difference be within a range of 200 mV to 400 mV, but this acceptable range can vary depending on system parameters, for instance the circuitry's active voltage range.

It should be understood that the hammer's impact force varies with the hammer's mass. In the presently-described embodiments, for example, the hammer comprises a solid member constructed of a phenolic thermoset plastic, but the hammer 54 is releasably secured within the solenoid 52, e.g. by set screws that secure a retractable retaining pin that retains the hammer, so that the hammer may be replaced as desired with hammers of the same shape and configuration but formed by different materials having different masses, so that the hammer mass, and therefore the impact force, may be controlled by the user through selection of a particular hammer. For example, hammers 54 may be made of polymer materials having greater or lesser mass or, for example, from brass or other metals having varying masses. Thus, if the user wishes to adjust the defect/no-defect peak-to-peak signal difference, the user may optionally replace the existing device hammer 54 with a hammer 54 having greater or lesser mass, depending on the direction of the desired adjustment.

Having replaced the hammer, the user executes the calibration process again to thereby move the output signal peak-to-peak voltage to just within the 500 mV peak-to-peak value, or to a buffer amount further below that level if desired, in the same manner as described above. Multiple hammer exchanges may be made. Still further, the application may provide an interactive method through the graphical user interface provided at display 102 by which the user may adjust the primary and, if present, secondary thresholds up or down as desired to accord with the signal results obtained from the impact hammer taps on the non-defect sample material. One or more of the methods described herein may be practiced within a calibration of a given device.

Upon successfully achieving the desired signal response, the user actuates a "save" button in the application's user interface, causing the application to save the calibrated hammer actuation or impact strength (and, if applicable, adjusted gain and threshold value(s) and/or hammer selection) in memory at unit 16 in association with an identifier (applied by the user as part of the calibration process) that corresponds to and uniquely identifies the test material under calibration. Thus, for any given test material, the system stores in memory a record that stores data items identifying the hammer impact strength, signal gain, primary and secondary threshold values, and hammer identity, in association with the given test material for the peak-to-peak amplitude test. If a user sets up a record for a given test material without performing a calibration, the application initially stores default gain, hammer impact force, thresholds, and hammer identities, and these remain in place until the user saves new values upon calibration. The system is then ready to be used for testing actual, in-use material of the same type as the calibration test material, in the manner as described herein.

As indicated above, however, the system may also be used in a mode by which the system analyzes acquired signals based on frequency. For example, and again assuming that data acquisition unit 14 acquires signals at a sampling frequency of 500 kHz and 1024 data points per hammer tap, the signal acquisition unit uploads analog data to data acquisition unit 14, which so digitizes the voltage-time signal. For each test data block, data acquisition unit 14 applies a windowing and fast Fourier transform (FFT) algorithm to thereby convert the signal to the frequency domain. A Hamming window is used in this process, in that it results in less ringing in the spectral values.

Figure 3:
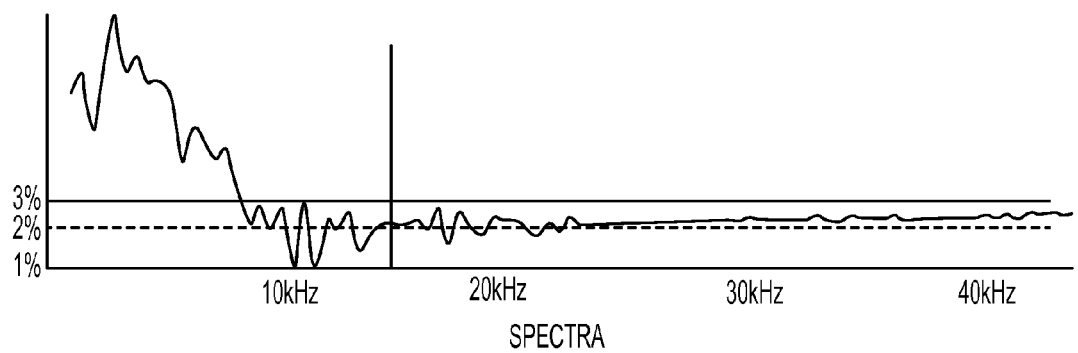
FIG. 3 is a graphical illustration of signals generated by the signal acquisition unit of FIG. 1B, processed by the data acquisition unit as in FIG. 1A for frequency domain-based analysis, and analyzed by the processing unit as in FIG. 1A.

FIG. 3 illustrates an example of such a signal, acquired with a microphone having an active range between about 2 kHz to about 25 kHz. Again, assume that the signal is acquired during calibration from a material known to have no defects. From testing and experience with materials of this type, it is known, for example, that defects result in a standing wave at a resonant frequency within a range of 2 kHz to about 15 kHz. Thus, the portion of the signal above 15 kHz in FIG. 3 is only or primarily the result of noise. In a calibration mode, the system application at unit 16 analyzes the test data block signal from 2 kHz to 15 kHz, finding the frequency at which the peak value occurs, in this instance about 2.5 kHz. Because this material is known to have no defects, the 2.5 kHz peak indicates that the resonant frequency of the standing wave produced in the test material between the surface at which the hammer strikes the material and the opposite surface, is 2.5 kHz.

The user may also test the device with a sample of the same material having a known defect. This also results in a signal analyzed by the system such as shown in FIG. 3, except that the peak resonant frequency occurs at a different frequency. The difference, or contrast, between the peak resonant frequency in the no-defect sample and the peak resonant frequency in the defect sample illustrates the scale of the magnitude of the frequency shift the system should be able to identify in distinguishing materials having no defects from those having defects. In examining later samples, the system will compare the detected peak resonant frequency with the stored calibrated (no-defect) frequency value, so that peak resonant frequencies that are within a calibrated threshold distance (in frequency) from the calibrated frequency value are considered not to identify defects, while those outside the threshold frequency distance identify defects. Thus, given the identified frequency difference between the two peak resonant frequencies in the calibration, the user can select a frequency threshold difference value within that distance that is just beyond a normal expected variance. As in the peak-to-peak amplitude/voltage example, however, it may be desired to have more separation between the non-defect peak sample resonant frequency and the defect peak sample resonant frequency, to assure that the variety of possible defects are detectable and distinguishable by the system. Thus, the user can adjust the preamplifier gain, hammer impact strength, and possibly hammer identity, in a similar manner as described above, and the user can then re-test the no-defect and defect samples, repeating the process until the two tests present an acceptable contrast between the defect and no-defect peak resonant frequencies. At this point, the user selects the threshold frequency difference and enters this value to the processor of unit 16 via a user interface screen presented at display screen 102.

Also in response to user instruction through the interface during the calibration, the system application at unit 16 measures the amplitude variation in the no-defect sample signal from 15 kHz to 25 kHz, determines the mean signal value and the standard deviation in the signal data from that mean value. The processor of processing unit 16 stores the no-defect sample resonant frequency (in this example 2.5 kHz) as the calibrated normal resonant frequency for the selected material, and also stores the mean noise value and the standard deviation, as well as the calibrated pre-amplifier gain, hammer impact strength, threshold value(s), and hammer identity as part of the calibration parameters for the corresponding test material under the frequency-based analysis test option.

Thus, as with the peak-to-peak calibration procedure, the user may conduct frequency-based calibration procedures with various materials, storing each set of calibration values in association with an identifier corresponding to a particular material. Moreover, the user may calibrate the same test material both for peak-to-peak amplitude-based and frequency-based analysis, storing both options at unit 16 in association with the material identifier so that the respective set of calibration parameters is stored in the test material record in association with the corresponding test option, so that when the user later selects one option or the other by which to test a given material, the system can pull the calibration parameters associated with the selected material and test option and configure the system according to the corresponding parameter instances. A user may wish to test the same material sample both under the peak-to-peak method and the frequency method.

Although the present discussion anticipates that an end-user may perform the calibration procedures discussed herein, these procedures may also be performed by the manufacturer as part of the manufacturing process, storing the relevant calibration data in the device in association with respective test material and test option identifiers, for later use of the device by the end-user.

As noted, when the end-user uses system 10 to test a given material, the user identifies the test material and the desired analysis option through the graphical user interface provided at screen 102. Upon receipt of the selection, processing unit 16 selects the calibration parameters associated with the selected material for the selected analysis option. For purposes of this discussion, assume the user selects the frequency option. When the user thereafter uses the system to test a material sample, and signal acquisition unit 12 provides the resulting voltage-time test data block signals to data acquisition unit 14, data acquisition unit 14 digitizes each test data block signal and applies the Hamming window and FFT algorithm to produce a signal such as is shown in FIG. 3. Data acquisition unit 14 forwards the resulting data to processing unit 16. The application at unit 16 then determines the peak resonant frequency and compares that frequency to the calibrated peak resonant frequency value. If a defect is present in the material, the detected peak resonant frequency will be different from the peak frequency expected if no defects are present by an amount at least as large as the stored calibration frequency difference. This occurs because a defect having a resolution within the range of the presently described embodiments will produce a peak response that is both of a different decibel level and at a different resonant frequency than results for the standing wave generated by the opposing side of the material. If the detected resonant frequency is offset from the calibrated peak resonant frequency by more than the calibrated frequency difference, processing unit 16 sends a signal to the data acquisition unit that causes the data acquisition unit to send a signal to the signal acquisition unit, causing the signal acquisition unit to actuate the red LED 72, indicating a defect.

In this embodiment, a secondary threshold frequency difference is not used, although it should be understood that a secondary threshold could be used, for example established as a predetermined distance away from the calibrated peak resonant frequency. In such an embodiment, if the detected peak resonant frequency is offset from the initial calibrated peak resonant frequency by an amount greater than the stored primary threshold difference, but not by more than the secondary threshold frequency difference, processing unit 16 sends a signal to data acquisition unit 14, which sends a signal to signal acquisition unit 12, causing signal acquisition unit 12 to actuate the yellow LED 72, indicating an intermediate defect. If the detected peak resonant frequency is offset from the calibrated peak resonant frequency by less than the initial, primary threshold frequency difference amount, processing unit 16 sends a signal to signal acquisition unit 12, via data acquisition unit 14, causing the signal acquisition unit to actuate the green LED 72.

Other tests may be applied to the frequency domain data. For example, during calibration of the system for multiple samples of the same material, where the samples have varying defects, the testing may reveal the occurrence of signal peaks at consistent frequencies respectively corresponding to various types of defects. The user may save these frequency markers within the memory of processing unit 16 through data entry via the graphical user interface at display screen 102. When the processing unit receives a test data block from data acquisition unit 14, the processing unit application locates the resonant frequency peak(s) and compares the corresponding frequency(ies) to the stored frequency markers. If the test data block has one or more peak resonant frequencies at or sufficiently close to corresponding stored frequency markers, the application determines that there is likely a defect and, accordingly, sends a signal to signal acquisition unit 12 via data acquisition unit 14 to activate the red LED 72. If there are no peak resonant frequencies at or close to a stored frequency marker, the application sends a signal to signal acquisition unit 12 to activate the green LED 72.

Still further, the application at processor 16 can determine the mean signal value in the test data block from 2 kHz to 15 kHz and compare that detected value to the calibrated mean signal value saved for the no-defect sample for the material under test. If the presently detected mean signal value is greater than the calibrated mean signal value by an amount greater than the calibrated standard deviation, this indicates the possible presence of a defect in the material under test, particularly for far side disbonds.

Varying embodiments of the system described herein use one or more of these tests in determining whether a defect is present in a material under test. For example, in some embodiments, the system uses only the peak resonant frequency shift test, while in other embodiments, the system detects a defect only if the frequency shift test indicates a defect and at least one of the frequency marker test and the mean signal value test also indicates presence of a defect, while in still further embodiments the system determines presence of a defect if any one of the three tests indicates a defect. Thus, it should be understood that various analyses may be implemented.

As indicated above, the user begins a test, whether in calibration mode or actual test mode, by actuating start/stop button 74. This causes circuitry on board 22 to energize the coil in solenoid unit 52, overcoming the internal spring bias to thereby move hammer 54 downward along axis 68 away from face 44 and toward the surface of the test material. In the presently-described embodiments in an automation mode, the circuitry at board 22 repeatedly actuates solenoid unit 52, so that solenoid unit 52 repeatedly drives hammer 54 downward along axis 68 to strike the test surface, and so that between such strikes or taps, the spring internal to the housing of solenoid unit 52 returns hammer 54 along axis 68 and away from the test material surface, in preparation for the next tap. The tap and return cycle occurs, for example, eight times per second, or at a 125 millisecond period. Because the electrical power used to drive solenoid unit 52 is drawn from the batteries secured to tray 84, the potential of those batteries (e.g. 7.6 v for rechargeable batteries, up to 14 v) defines the baseline power at which hammer 54 may be driven to tap the test material surface. The signal acquisition unit processor, on board 22, controls the duty cycle of that 125 millisecond period to control, through pulse width modulation, the power applied to the hammer by solenoid 52. In the presently-described embodiment, the processor controls the control circuitry so that the duty cycle is variable between 2% and 50%. That is, the duty cycle is variable so that the power control circuitry applies the battery across the solenoid coil within a range of 2.5 milliseconds to 62.5 milliseconds out of the 125 millisecond period. As should be understood in view of the present disclosure, the high part of the duty cycle, i.e. the percentage of the duty cycle at which power is applied to the solenoid coil, contributes directly to the force with which the solenoid drives hammer 54 downward along axis 68. Thus, by controlling the duty cycle within the 2% to 50% variable range, the device directly varies the hammer's impact force.

In that regard, the signal acquisition unit processor, having control over the solenoid's impact force, drives LED display 26 to display a number indicating the signal acquisition unit's hammer force (which corresponds to duty cycle setting) at any given time. For example, the programming of the signal acquisition unit processor may convert the 2% to 50% duty cycle scale to a scale of 0 to 100, with 2% duty cycle corresponding to 0 and 50% corresponding to 100. At any time during the system's operation, and as described above, the user can change the impact hammer's impact force through actuation of buttons 30 or 32 on the signal acquisition unit housing. These buttons are connected to a switch system that communicates with the signal acquisition unit microprocessor. The processor's programming is configured to recognize actuations of button 30 as a request from the user to decrease the solenoid power, and to interpret actuations of button 32 as a request to increase the solenoid power. Thus, by pressing button 30, the user instructs the signal acquisition unit processor to lower the solenoid power duty cycle, thereby lowering the power at which hammer 54 taps the test material. Correspondingly, the user's actuation of button 32 instructs the signal acquisition unit processor to increase the solenoid duty cycle and thereby increase the hammer impact force. As the user moves the impact power up or down, the signal acquisition unit processor changes the displayed impact power rating on display 26 to maintain correspondence with the duty cycles selected by the user.

The signal acquisition unit may also automatically adjust the solenoid's duty cycle, and therefore the hammer's impact force, based on the output of an inertial measurement unit (IMU) mounted on board 22. The construction and operation of inertial measurement units should be understood, and is therefore not discussed in detail herein. As should be understood, an IMU outputs data representative of the device's pitch, roll, and yaw with respect to an initial condition, e.g. in which hammer 54 and its axis 68 are vertically aligned, the hammer distal end is directed downward, and the plane defined by the distal ends of feet 42 and 48 is horizontal.

Given a particular hammer mass, solenoid duty cycle, gap distance, and hammer stroke, as described above, the force at which hammer 54 strikes the material test surface will also vary correspondingly with gravitational effects over the signal acquisition unit's three dimensional orientation. The orientation's most positive effect corresponds to the greatest hammer force when axis 68 is directly vertical and when the distal end of hammer 54 is facing downward. Conversely, the orientation's most negative impact on hammer impact strength occurs when axis 68 is vertical but the distal end of hammer 54 is pointing directly upward. The gravitational effect varies between these extremes over the various pitch, roll, and yaw variations between straight up and straight down. These variations are determined through calibration and are stored in a lookup table accessible by the signal acquisition unit microprocessor in memory. The table stores incremental pitch, roll, and yaw ranges, or zones, between the zero degree and 180 degree extremes, and respectively associates the increments with adjustments in solenoid duty cycle as determined by the calibration process.

When the user begins a test by actuating start/stop button 74, the signal acquisition unit processor detects the pitch, roll, and yaw output of the IMU, selects the duty cycle adjustment corresponding to the stored pitch, roll, and yaw increment zone within which the actual pitch, roll, and yaw falls, and adjusts the calibrated solenoid duty cycle accordingly.

As described above, the hammer's impact force varies with the hammer's mass. In the presently-described embodiments, for example, the hammer comprises a solid member constructed of a phenolic thermoset plastic, but hammer 54 is releaseably secured within solenoid 52, by set screws that secure a retaining pin that retains the hammer, so that the hammer may be replaced as desired with hammers of the same shape and configuration but formed by different materials having different masses, so that the hammer mass, and therefore impact force may also be controlled by the user through selection of a particular hammer. For example, hammers 54 may be made of polymer materials having greater or lesser mass or, for example, from brass or other metals having varying masses.

The discussion above has assumed that the test material surface is perfectly planar. Often, however, the test material surface will be curved, for example as is the case for materials used in the construction of many aircraft components. Surface curvature, whether convex or concave, or other deviations from a perfectly planar surface can cause variations in the distance between the receiving transducer surface of microphone 60 and the test material surface as the signal acquisition unit is moved to different positions on the test material surface during use. Such surface height variations may cause the system's response to vary from what it would be with a planar sample of the test material (assuming the system was calibrated with a planar material). For example, assume the signal acquisition unit is placed over a portion of the test material surface that has a high point. The gap between the hammer and the microphone transducer is less than it would be if the test surface were flat, causing the hammer to strike the surface with a higher force and the microphone to receive the resulting acoustic signal at a greater intensity. On the other hand, depressions in the test material surface can have the opposite effect.

Where the signal acquisition unit is intended for use with test materials having generally known curvatures, the device may be constructed to minimize distances between adjacent bolsters 42/48 to thereby minimize variability in the gap between the test material surface and the microphone transducer and hammer Referring again to FIG. 1B, consider each of bolsters 42 and 48 to define a longitudinal axis extending parallel to axes 66 and 68 and extending through the center of the respective bolster. Considering respective distances, in directions transverse to these axes, between the axes of bolsters 42 (0.44 inches in one embodiment), between the axes of bolsters 48 (again, 0.44 inches in the same embodiment), between the axes of the respective bolsters 42 and 48 on clamshell half 17a (2 inches in the same embodiment), and between the axes of bolsters 42 and 48 on clamshell half 17b (2 inches in the same embodiment), and the two distances between the axes of the diagonally arranged bolsters 42 and 48, the housing formed by clamshell halves 17a and 17b, the placement of the bolsters in the housing, and the maximum hammer travel (⅜ inches in the same embodiment) are selected so that when the signal acquisition unit is used on the test material, the material's convex surface formations do not extend sufficiently far into the gap between the planar surface defined by the bolster distal ends and the microphone/hammer to invalidate the system's calibration and so that the material surface's concave formations do not move sufficiently far from the hammer and the transducer from that ideal planar surface to invalidate the original calibration. Where a material has areas of curvature that negate the device's original calibration to a flat surface, the system may be separately calibrated to the same material, but on a sample of such material having the expected curvature. Such calibration may result, for instance, in hammer impact strengths, gain, and/or hammer identities or other calibration parameters that differ from those parameters determined by an original calibration for the same material in a flat configuration. This calibration is then separately stored in the device, as described above, so that the user can select the stored calibration for the given curved surface when the need arises to test such a surface. Also, it should be understood that where the test material surface curves in only one dimension, it may be possible to orient the signal acquisition unit on test material so that the test occurs on a surface with lesser effective curvature.

The present system may also be used to record test data in association with relative spatial reference information. The system stores each test result in association with the underlying signal data that generated the result and with three dimensional position data that identifies a point at which the test data was acquired within a three dimensional coordinate system common to the position data for the other test points taken on the same test material surface. A three dimensional scan of the test surface may also be acquired, in association with the same three dimensional coordinate system, and provided to an independent computer system that may, in turn, display the test material surface with indicators identifying the positions on the surface at which the tests were taken, with icons (which may be color coded correspondingly to the red/green or red/yellow/green presentation of LEDs 72) indicating the respective test results (i.e. pass, intermediate defect, and significant defect).

More specifically, prior to executing a series of tests on a given test material, the user mounts a local positioning system, in this instance a three dimensional scanner device, in a fixed position with respect to and proximate the test material so that the scanning device images the entire area of the material surface that will be tested. An example of such a scanner is the three-dimensional infrared scanner sold under the name FREESCAN by NDT Consultants Limited, of Coventry, United Kingdom. The scanner illuminates the test material surface over which an active reflector is moved, receives reflected data at two cameras that are offset from each other within the scanner system, and based on triangulation of the reflected data received by the cameras, creates data describing a portion of the test material surface within a three dimensional coordinate system. Thereafter, the scanner monitors the cameras, which are infrared-sensitive, having the test surface in their fields of view. When the user, having now placed the signal acquisition unit at a given position on the test material surface within the scanner field of view to conduct a test, actuates button 74 to start that test, the signal acquisition unit's processor actuates infrared transmitter 70 on the top of unit 12, thereby causing transmitter 70 to emit an infrared signal detectable by the scanner cameras. The scanner cameras detect the signal and determine the position of the infrared transmitter in the same three dimensional coordinate system in which the test surface material scan is defined.

The scanner then transmits the three dimensional coordinates to processing unit 16, via a short-range wireless communication between the two devices, for example under the BLUETOOTH protocol. Having received the position information from the scanner, and having also received the test data from the signal acquisition unit and the data acquisition unit, as described herein, from the test that generated the position data, the processing unit stores the test data, the test data results (i.e. whether the test data indicated presence of a defect according to a methodology such as described above), and the position data in association with each other in a discrete data record or file in memory at the processing unit. The user then moves unit 12 to the next position on the test material at which it is desired to test for defects. The process repeats, such that processing unit 16 acquires position data and test data for the second test position. This process repeats for as many tests as the user wishes to make. As a result, the processing unit has stored each incremental portion of test data, the result of the application of the test data to the defect identification analysis described herein, and the position data, for each respective test point on the test material surface. The association of each set of test point data with a respective position in a common three dimensional coordinate system, in which the scan image of the test material surface is also located, allows an independent computer system to create an image of the three dimensional test material surface scan, correlate the stored test data to positions on the scan surface, and indicate on a displayed image of the scanned test material surface whether a defect occurred at each respective position. The independent computer system, which receives the stored test data (including the three-dimensional position data) from processing unit 16, e.g. via a wireless connection as discussed above or other method such as via the processing unit's USB port or a removable memory such as a microSD card, and the test material scan data from the scanning device, presents an image on a display screen of the test surface, with the indication at each point on that surface at which a test has occurred, whether the test passed or failed, and if failure occurred whether the defect was intermediate or significant. Icons can be used as desired to represent such conditions at each surface point. This provides the user viewing the screen to visually and intuitively identify the location of each test result on the surface image.

Accordingly, system 10 provides information to the user regarding possible defects in the material, not only through real-time actuation of LEDs 72 and the display on screen 102, indicating to the user whether a defect has occurred, but also by downloading to a remote computing device a data set that locates the test data within a common three dimensional reference system so that the test data can be located on an image of the test material surface itself.

FIG. 2 illustrates the general electronic organization of the circuitry of signal acquisition unit 12 that is mounted on board 22. A processor 118 drives LED display 26 via an LED driver (not shown). A membrane switch, indicated generally at 120, defines up and down buttons 30 and 32 (driven by field effect transmitters on board 22), start/stop button 74, and LEDs 72. Again, microprocessor 118 drives LEDs 72 via appropriate LED drivers.

Microprocessor 118 drives solenoid unit 52 via a boost converter 122 that is powered by the batteries stored at tray 84. Microprocessor 118 also communicates with IMU 124 and drives infrared transmitter 70, in the manner as described herein. As described above, infrared transmitter 70 communicates with local positioning system 126 via an infrared signal communication path, indicated at 129. Local positioning device 126 communicates with processing unit 16 via BLUETOOTH wireless connection indicated at 130.

FIG. 2 also illustrates the general electronics configuration of data acquisition unit board 76. Microprocessor 118 and microphone 60 of the signal acquisition unit communicate with a microprocessor 132 of the data acquisition unit via cable connection 134 between connectors 128 and 40 on the data acquisition unit and the signal acquisition unit, respectively. The signal acquisition unit drives the cable communication to the data acquisition unit via preamplifier 136. Upon detecting the incoming signal from cable 134, an input selector relay 138 at unit 14 directs the signal to an amplifier module 140 and an analog-to-digital converter 142. The digital data is stored in a static random access memory 144, from which microprocessor 132 retrieves the data, detects the beginning of test data blocks, performs post-processing, if any (for example, by applying a Hamming window and fast Fourier transform in embodiments in which signal analysis is conducted in the frequency domain), and outputs the digitized test data blocks to processing unit 16 via a high speed USB device 146 and cable that passes through conduit line 98.

Figure 4:
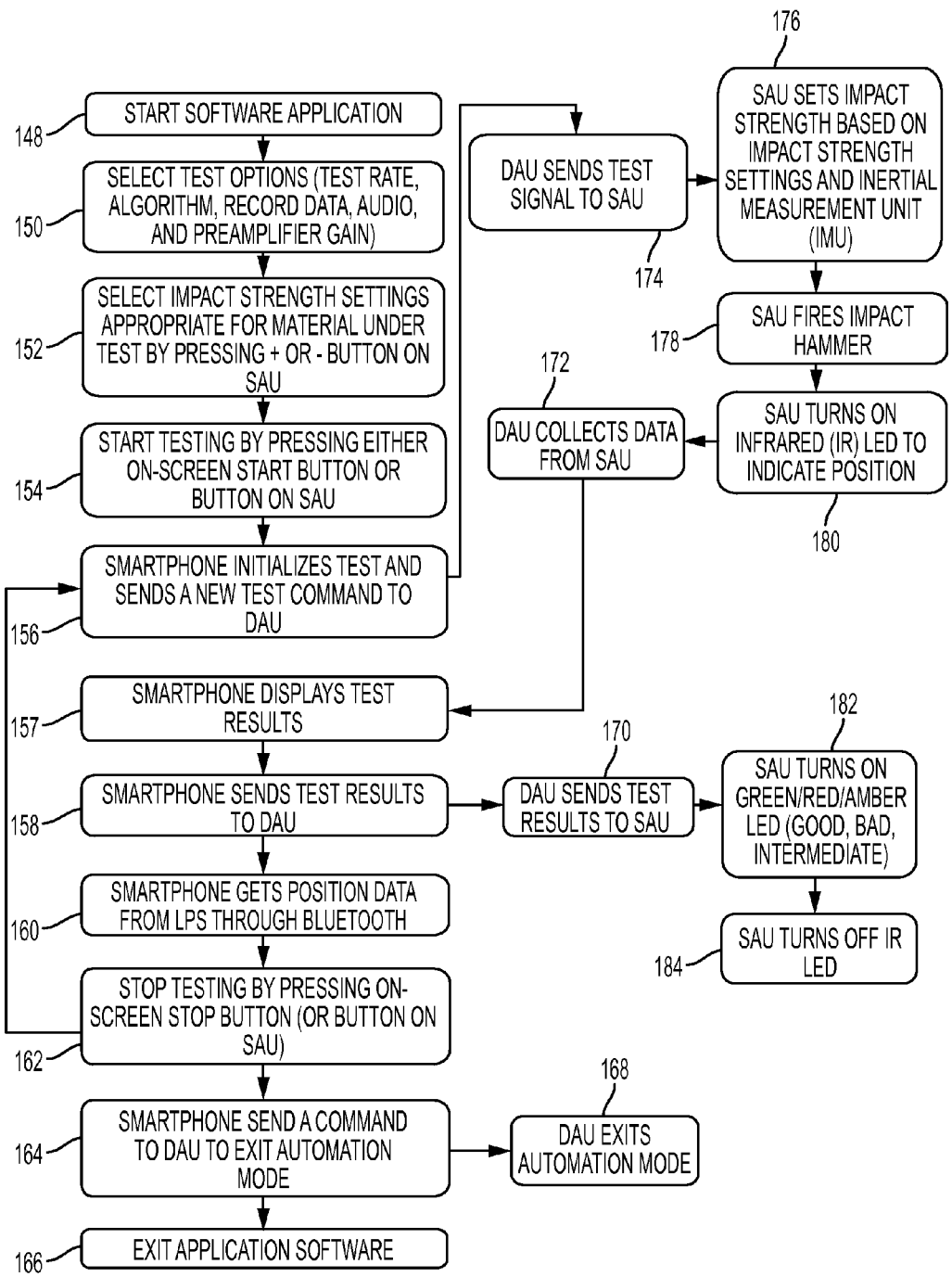
FIG. 4 is a flow diagram of operations of the data acquisition unit, processing unit, and signal acquisition unit of FIGS. 1A and 1B.

FIG. 4 (and also with reference to the system components described with respect to FIGS. 1 and 2) illustrates the operation of system 10, in sequence form. At 148, a user has actuated on/off button 74 of the data acquisition unit, sending a signal to microprocessor 132 that causes the microprocessor to send a signal via USB device 146 and cable 98 to processing unit 16, causing the processing unit to actuate a power up sequence. Alternatively, the user can actuate the power-up mechanism on the smartphone processing unit itself. In either instance, actuation of device 16 initiates the application program that resides on unit 16.

At 150, the processing unit application program presents a graphical user interface at screen 102 through which the user may select various options for conducting the test. For example, the user may select the test rate, i.e. the rate that hammer 54 impacts the surface—eight times per second in the example described above, or for example ten times per second. The user may also select the number of data points (e.g. 1024, 2048, or 4096) for which the circuitry of data acquisition unit 14 collects at each hammer impact, and the rate at which those data points are sampled (e.g. 500,000 samples per second in the examples above, or as otherwise selected by the user at step 150). The user may also select the test material and the analysis algorithm that will be used to analyze the data acquired by the system acquisition unit and processed by the data acquisition unit. As described in more detail above, for example, the algorithm may analyze the test data based on peak-to-peak voltage or by resonant frequency shift. The user may also select whether processing unit 16 not only visually displays the test output data on screen 102 and instructs the signal acquisition unit to display the result via LEDs 72, but also to store the test data and position data at processing unit 16 for later download to a remote computing system. Audio effects may be provided, for example issuing varying audio signals detectible by the human operator in response to test data, corresponding to the green, yellow and red LEDs 72. The user may also select whether the test will be in a single tap mode, in which the hammer makes only a single impact of the test material, or automation mode, in which the hammer continuously impacts the test material surface, until the user instructs the test to end.

As described above, the user will have determined the appropriate hammer impact strength, hammer identity, threshold value(s), and/or signal amplifier gain to apply to test signals from the particular material under test, for the peak-to-peak test, and normal resonant frequency, mean noise value, standard deviation, gain, hammer impact strength, hammer identity, and threshold value, for the frequency-based test for the same material. These setting or parameter records may be stored in a lookup table in memory at processing unit 16, and at step 150 the graphical user interface in this instance provides a lookup option by which the user may select an identifier corresponding to the particular test material, and then provides an option by which the user selects the test analysis option for the selected material. Upon receiving the user's selections for these options from the user interface, the processor of processing unit 16 selects the corresponding set of calibration parameters. As noted above, for example, the calibration data includes hammer identity, and the unit 16 processor drives (via the application) the user interface to display the hammer identity from the selected calibration data, so that the user may install the correct hammer for the test. To set the gain identified in the record, processing unit 16 sends (at step 156) a corresponding signal to SAU processor 118 via DAU processor 132 at step 174, which in turn configures preamplifier 136 to the proper gain at step 176. To set the hammer impact strength, processing unit 16 sends (at step 156) a corresponding signal to SAU processor 118 via DAU processor 132 at step 174 so that processor 118 thereafter actuates the solenoid at step 176 at the desired strength level when impacts are required in the steps described below. Alternatively, as indicated at 152, the application at processing unit 16 may drive the graphical user interface at display 102 to display the hammer impact strength and gain from the calibration data for the test material and test analysis option the user selects, so that the user may manually configure the SAU to the appropriate hammer impact strength through actuation of buttons 30 and 32 and manually configure the gain through up/down buttons available on user interface 102 (causing the processing unit to then send instructions to SAU processor 118 at 174 to correspondingly configure preamplifier 136 at 176). Processing unit 16 uses the remaining calibration parameters in analyzing the test measurement signals as described herein.

Even where the processing unit automatically sets the system according to the calibration data, the user may, at step 152, further adjust the hammer impact strength through actuation of buttons 30 and 32 on the signal acquisition unit (to thereby set the solenoid duty cycle), if further adjustments are desired. Also at 152, the user may select and install a desired hammer 54 based on the mass and stroke length appropriate for the material under test, as determined by calibration.

At 154, the user has placed the signal acquisition unit in the operative position on a test material (see FIG. 5), so that bolsters 42 and 48 rest upon the test material surface, and begins a test either by actuating a start button provided through the user interface on touch screen 102 or by actuating start/stop button 74 on the signal acquisition unit. If the user actuates start/stop button 74 on unit 12, microprocessor 118 forwards a corresponding signal to microprocessor 132 of the data acquisition unit as described above. Microprocessor 132 then forwards the signal to processing unit 16. If the user actuates the test through the user interface screen, processing unit 16 receives the instruction directly. Following either event, processing unit 16 responds, at 156, by sending an instruction to processor 132 of the data acquisition unit via cable 98, notifying the data acquisition unit that a test has begun and providing the signal gain settings to apply to the digitized data.

At 174, microprocessor 132 forwards a notice signal to microprocessor 118 of the signal acquisition unit via cable 134, instructing the signal acquisition unit to begin the test. The calibration data for hammer impact strength and gain selected and/or received at steps 150 and 152 are provided to microprocessor 118 at this time via this transmission. At 176, microprocessor 118 reads the output of IMU 124, determining the IMU's pitch angle, roll angle, and yaw angle and converting this information to the orientation of signal acquisition unit 12. Accordingly, at 176, microprocessor 118 sets the duty cycle of boost converter 122 to the hammer impact strength duty cycle selected by the user or identified in the selected calibration data, adjusted based on the lookup table accessed by processor 118 in response to the orientation of signal acquisition unit 112 as indicated by IMU 124.

At 178, microprocessor 118 actuates solenoid 52 via boost converter 122. If the user selected a single tap test at step 150, the SAU actuates the impact hammer only once. If the user selected an automation test at step 150, the SAU actuates the impact hammer solenoid 52 at a rate of eight impacts per second, at the selected duty cycle, until a stop signal is received. Accordingly, while the system is in automation mode, the user may pick up and move the signal acquisition unit from place to place on the test material, or may simply slide the SAU across the test material surface, collecting test data in either case without having to repeatedly activate the start button to begin the hammer taps. Since the data acquisition unit collects test data blocks from the resulting movement signal in 1024 (or other selected) data point groups beginning with detection of a measurable signal portion, the DAU and processing unit will acquire and accumulate test data as it is generated, regardless of the method by which the hammer is actuated or by which the SAU is moved over the test material surface.

At 180, processor 118 drives infrared transmitter 70 to transmit infrared signal 129 to the local positioning system 126, causing local positioning system 126 to determine the position of infrared transmitter 170 within a predetermined three-dimensional coordinate system and to transmit the position data to processing unit 16 via wireless connection 130.

Upon sending processor 118 the instruction to begin the test, microprocessor 132 of the data acquisition unit begins repeatedly monitoring memory 144 for the arrival of test data from the signal acquisition unit. When microphone 60 receives a responsive audio signal, the microphone outputs the data to preamplifier 136, which amplifies and transmits the data to input selector relay 138 via cable connection 134. As described above, the test data is amplified at 140, converted to a digital signal at 142, and stored in memory at 144. Accordingly, at step 172, microprocessor 132 identifies the digitized test data blocks from the data at memory 144 and transmits the test data blocks to processing unit 16 via connection 98. Processing unit 16 applies the selected test algorithm to the test data received from the data acquisition unit, at step 172. At 157, processing unit 16 displays information at touch screen 102 through the user interface, indicating whether the test for each test data block results in an indication of no defect, an intermediate defect, or a significant defect. At 158, processing unit 16 sends information corresponding to the test result to processor 132 of the data acquisition unit via connection 98. At 170, processor 132 forwards the information to processor 118 via cable connection 134. At 182, processor 118 identifies from the received information whether the test result indicated no defect, an intermediate defect, or a significant defect and drives LEDs 72 accordingly via membrane switch 120. At 184, microprocessor 118 deactivates infrared transmitter 70.

At 160, processing unit 16 receives the position data associated with the test from local positioning system 126, via wireless connection 130. As described above, processing unit 16 stores the test data received from signal acquisition unit and data acquisition unit 14 in association with the corresponding position information associated with the test so that the data, so associated and also associated with the test result, can be downloaded to a remote computer.

At 162, the user indicates that the test has ended by actuating start/stop button 74 on signal acquisition unit 12 or by actuating a corresponding button through the user interface via touch screen 102. If the system is in a single tap test mode, no further instructions to the data acquisition unit are needed, and the application proceeds directly to an exit step at 166. If the system is in automation mode, however, receipt of the step command at 162 causes processing unit 16 to send another initialization signal to data acquisition unit processor 132, and therefore signal acquisition unit processor 118, at 164, and data acquisition unit 12 deactivates solenoid 52, thereby stopping the hammer taps, at 168. The application then exits the test routine at step 166. The system is, therefore, prepared for a next test so that when the user places signal acquisition unit 12 at the next desired test position on the test material and begins a test by activating button 74 or a corresponding button at the user interface at screen 102, the test procedure described herein repeats.

The software application at processing unit 16 may act as an intermediary between the user and/or other computers and the basic computer resources of processing unit 16, boards 22 and 76, and processors 132 and 118, as described, in suitable operating environments. Such software applications include one or both of system and application software. System software can include an operating system, which can be stored on processing unit 16, and also processors 118 and 132, that acts to control and allocate resources of these computer systems. The application software takes advantage of management resources by system software through program modules and data stored on either or both of system memory and other memory sources, for example, mass storage.

Moreover, it will be understood from the present disclosure that the functions ascribed to processing unit 16, processor 132, and processor 118 may be embodied by computer-executable instructions of a program, for example the application software and other programs discussed herein, that run on one or more of these computers. Generally, program modules include routines, programs, components, data structures, etc. that perform particular tasks and/or implement particular abstract data types. Moreover, those skilled in the art will appreciate that the system/methods may be practiced with other computer system configurations, including single-processor, multi-processor, or multi-core processor computer systems, as well as personal computer and hand-held computing devices, microprocessor-based or programmable consumer or industrial electronic, and the like. Aspects of these functions may also be practiced in a distributed computer environment where tasks are performed by remote processing devices that are linked through a communications network. However, some aspects of the claimed subject matter can be practiced on stand-alone computers.

Modifications and variations to the particular embodiments of the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to be limitative of the invention so further described in such appended claims.

What is claimed is:

1. A device for testing a test material for defects within the test material, the device comprising:
   a housing;
   an acoustic broadband transducer housed by the housing;
   an engagement portion of the housing defined with respect to the acoustic broadband transducer so that a distal end of the engagement portion defines a surface that is offset from a receiving portion of the acoustic broadband transducer;
   an impact member defining an impact portion and being housed by the housing so that the impact portion is movable from a retracted position to the surface, wherein the surface and the receiving portion of the acoustic broadband transducer are disposed with respect to each other so that the acoustic broadband transducer is capable of acquiring acoustic waves from a test material at the surface, wherein the acoustic waves arise from impact of the impact portion of the impact member with the test material upon movement of the impact portion of the impact member to the surface;
   a processor system in communication with the impact member and the acoustic broadband transducer so that the processor system, in response to receipt of an actuation signal, actuates the impact member to drive the impact portion from the retracted position to the surface and so that the processor system receives a first output signal from the acoustic broadband transducer corresponding to the acoustic waves that arise from impact of the impact portion with the test material at the surface; and
   an inertial measurement unit secured to the housing in a predetermined orientation so that the inertial measurement unit measures the housing's spatial orientation, wherein the inertial measurement unit is in communication with the processor system so that the inertial measurement unit outputs information to the processor system corresponding to the spatial orientation, and wherein the processor system is configured to adjust actuation of the impact member responsively to the information to offset gravitational variance corresponding to spatial orientation in impact of the impact portion to the test material.

2. The device as in claim 1, wherein the engagement portion comprises a plurality of bolsters extending from the housing so that respective distal ends of the bolsters define the surface.

3. The device as in claim 2, wherein the bolsters include respective roller bearings at the respective distal ends.

4. The device as in claim 2, wherein the processor system is configured to compare a magnitude level of the first output signal to a predetermined level corresponding to possible existence of a defect in the test material.

5. The device as in claim 4, wherein the processor system is configured to determine possible presence or absence of the defect based upon comparison of the magnitude level of the first output signal to the predetermined level.

6. The device as in claim 5, further comprising a display in communication with the processor system.

7. The device as in claim 6, wherein the processor system is configured to control the display to indicate the possible presence or absence of the defect.

8. The device as in claim 2, wherein the respective distal ends define an area within the surface having a first dimension and a second dimension orthogonal to the first dimension, and wherein the first dimension is about 0.44 inches and the second dimension is about two inches.

9. The device as in claim 2, further comprising a data port secured in the housing and in communication with the processor system, wherein the data port is disposed on a surface of the housing transverse to the surface defined by the distal ends of the bolsters.

10. The device as in claim 2, wherein the surface is offset from the receiving portion of the acoustic broadband transducer by a distance at which the acoustic broadband transducer is capable of acquiring to the acoustic waves across an air gap.

11. The device as in claim 2, wherein the processor system is configured to respond to receipt of the actuation signal to actuate the impact member to repeatedly drive the impact portion from the retracted position to the surface.

12. The device as in claim 2, wherein the processor system is configured to respond to receipt of the actuation signal to actuate the impact portion to repeatedly drive the impact portion from the retracted position to the surface at a rate of at least about eight cycles per second.

13. The device as in claim 12, wherein the processor system is configured to respond to receipt of the actuation signal to actuate the impact member to repeatedly drive the impact portion from the retracted position to the surface at a rate within a range of about eight cycles per second to about ten cycles per second.

14. The device as in claim 1, wherein the acoustic broadband transducer is an electronic condenser transducer.

15. The device as in claim 10, comprising a microphone that contains the acoustic broadband transducer and wherein a system comprising the processor system and the microphone has a resolution capable of detecting defects having a minimum dimension of about 0.125 inches in a plane perpendicular to a direction of travel of mechanical waves generated by the impact member in the test material.

16. The device as in claim 14, comprising a microphone that contains the acoustic broadband transducer and wherein a system comprising the processor system and the microphone has a resolution capable of detecting defects having a minimum dimension of about 0.125 inches in a plane perpendicular to a direction of travel of mechanical waves generated by the impact member in the test material.

17. A method for testing a test material for defects within the test material, comprising the steps of:
providing a test device comprising
a housing,
an acoustic broadband transducer housed by the housing,
an engagement portion of the housing defined with respect to the acoustic broadband transducer so that a distal end of the engagement portion defines a surface that is offset from a receiving portion of the acoustic broadband transducer,
an impact member defining an impact portion and being housed by the housing so that the impact portion is movable from a retracted position to the surface, wherein the surface and the receiving portion of the acoustic broadband transducer are disposed with respect to each other so that the acoustic broadband transducer is capable of acquiring acoustic waves from the surface;
measuring the housing's spatial orientation;
placing the test device so that the engagement portion engages a test material at the surface;
moving the impact portion of the impact member to the surface so that the impact portion of the impact member impacts the test material, responsively to the spatial orientation to offset gravitational variance corresponding to spatial orientation in impact of the impact portion to the test material; and
acquiring, via the acoustic broadband transducer, acoustic waves from the test material, where the acoustic waves arise from impact of the impact portion of the impact member with the test material.

18. The method as in claim 17, further comprising determining possible existence of a defect in the test material in response to information acquired from the acoustic broadband transducer corresponding to the acoustic waves acquired at the acquiring step.

19. The method as in claim 18, wherein the determining step comprises comparing a magnitude level of an output signal from the acoustic broadband transducer corresponding to the acoustic waves to a predetermined level corresponding to possible existence of a defect in the test material.

20. The method as in claim 17, wherein the acquiring step comprises acquiring, via the acoustic broadband transducer, the acoustic waves across an air gap.

21. The method as in claim 17, wherein the moving step comprises repeatedly driving the impact portion from the retracted position to the surface.

22. The method as in claim 17, wherein the moving step comprises repeatedly driving the impact portion from the retracted position to the surface at a rate of at least about eight cycles per second.

23. The method as in claim 17, wherein the moving step comprises repeatedly driving the impact portion from the retracted position to the surface at a rate within a range of about eight cycles per second to about ten cycles per second.

* * * * *